United States Patent [19]

Alexander et al.

[11] 3,948,939

[45] Apr. 6, 1976

[54] 9-ACYL-1,2,3,4-TETRAHYDROCARBAZOLE-3 AND 4-CARBOXYLIC ACIDS

[75] Inventors: Ernest John Alexander, East Greenbush; Aram Mooradian, Schodack, both of N.Y.

[73] Assignee: Sterling Drug Inc., New York, N.Y.

[22] Filed: Oct. 15, 1974

[21] Appl. No.: 514,767

Related U.S. Application Data

[63] Continuation-in-part of Ser. No. 314,099, Dec. 11, 1972, Pat. No. 3,905,998, which is a continuation-in-part of Ser. No. 200,205, Nov. 18, 1971, Pat. No. 3,758,496, which is a continuation-in-part of Ser. No. 42,620, June 2, 1970, Pat. No. 3,687,969.

[52] U.S. Cl. .............................................. 260/315
[51] Int. Cl.² ....................................... C07D 209/86
[58] Field of Search .................................... 260/315

[56]  References Cited
UNITED STATES PATENTS
3,535,326   10/1970   Yamamoto et al. ................ 260/315

OTHER PUBLICATIONS
J. Heterocyclic Chemistry, 7: pp. 239–241, (1970), Allen.

*Primary Examiner*—Sherman D. Winters
*Attorney, Agent, or Firm*—Frederik W. Stonner; B. Woodrow Wyatt

[57]  ABSTRACT

Novel 9-aroyl-1,2,3,4-tetrahydrocarbazoles bearing a carboxy substituent at position 3 or 4 and corresponding esters having antiinflammatory activity, the preparation thereof and novel intermediates therefor are described.

41 Claims, No Drawings

9-ACYL-1,2,3,4-TETRAHYDROCARBAZOLE-3 AND 4-CARBOXYLIC ACIDS

COMPOUNDS AND PROCESSES

This application is a continuation-in-part of copending application Ser. No. 314,099, filed Dec. 11, 1972, now U.S. Pat. No. 3,905,998, issued Sept. 16, 1975, in turn a continuation-in-part of Ser. No. 200,205, filed Nov. 18, 1971, now U.S. Pat. No. 3,758,496, issued Sept. 11, 1973, in turn a continuation-in-part of Ser. No. 42,620, filed June 2, 1970, now U.S. Pat. No. 3,687,969, issued Aug. 29, 1972.

This invention relates to new tetrahydrocarbazoles and more particularly to a new class of 1,2,3,4-tetrahydrocarbazoles and to processes for their preparation. More specifically this invention relates to 9-carboxylic acyl-1,2,3,4-tetrahydrocarbazoles bearing at either the 3 or 4 position of the tetrahydrocarbazole ring a carboxy substituent, and corresponding esters.

In one aspect of the invention there are provided compounds having the formula

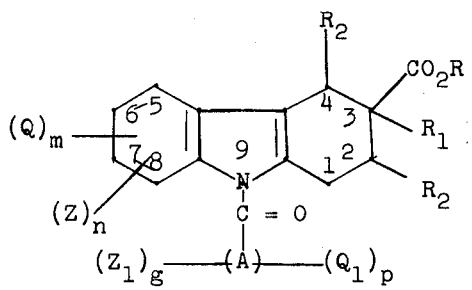

wherein (A) represents phenyl, naphthyl, 2-thienyl, or cyclohexyl; Q and $Q_1$ represent substituents selected from lower-alkyl, phenyl-lower-alkyl, lower-alkoxy, phenyl-lower-alkoxy, phenoxy, phenyl, di(lower-alkyl)amino, lower-alkanoylamino, trihalomethyl, trihalomethoxy, halo and hydroxy, where phenyl is unsubstituted or substituted by from one to three of the same or different substituents selected from lower-alkyl, lower-alkoxy, trihalomethyl and halo; Z and $Z_1$ represent substituents selected from lower-alkylthio, lower-alkylsulfinyl, lower-alkylsulfonyl, amino, and nitro; m represents an integer from 0 to (3-n) inclusive; p represents an integer from 0 to (3-g) inclusive; n and g represent integers from 0 to 1 inclusive; R represents hydrogen, lower-alkyl, 4-acetamidophenyl, lower-alkanoyloxymethyl, benzoyloxymethyl or benzoyloxymethyl substituted on phenyl by from one to two of the same or different substituents selected from lower-alkyl, lower-alkoxy, trihalomethyl, nitro and halo; and $R_1$ and $R_2$ each represent hydrogen or methyl, at least one of which is hydrogen; or $(Q)_m$ taken together with $(Z)_n$, or $(Q_1)_p$ taken together with $(Z_1)_g$ represent methylenedioxy attached to adjacent carbon atoms.

In another aspect of this invention there are provided compounds having the formula

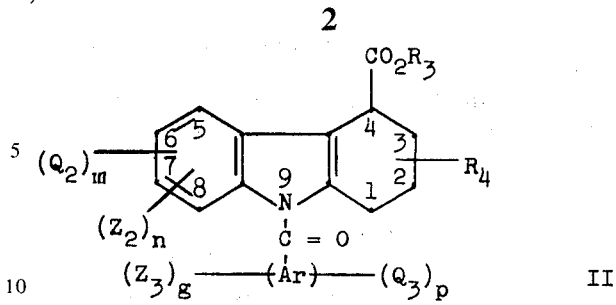

wherein (Ar) represents phenyl or naphthyl; $Q_2$ and $Q_3$ represent substituents selected from lower-alkyl, phenyl-lower-alkyl, lower-alkoxy, phenyl-lower-alkoxy, phenoxy, phenyl, di(lower-alkyl)amino, trihalomethyl, trihalomethoxy, halo and hydroxy, where phenyl is unsubstituted or substituted by from one to three of the same or different substituents selected from lower-alkyl, lower-alkoxy, trihalomethyl and halo; $Z_2$ and $Z_3$ represent lower-alkylthio; m represents an integer from 0 to (3-n) inclusive; p represents an integer from 0 to (3-g) inclusive, n and g represent integers from 0 to 1 inclusive; $R_3$ represents hydrogen, lower-alkyl, 4-acetamidophenyl, lower-alkanoyloxymethyl, benzoyloxymethyl or benzoyloxymethyl substituted on phenyl by from one to two of the same or different substituents selected from lower-alkyl, lower-alkoxy, trihalomethyl, nitro and halo; and $R_4$ represents hydrogen or methyl; or $(Q_2)_m$ taken together with $(Z_2)_n$, or $(Q_3)_p$ taken together with $(Z_3)_g$ represent methylenedioxy attached to adjacent carbon atoms.

It will be understood, here and throughout the specification, that when $R_4$ represents methyl, said methyl can occur at any one of the positions $C_1$, $C_2$, $C_3$ or $C_4$ of the 1,2,3,4-tetrahydrocarbazole ring.

The compounds of the invention having formulas I and II were found to have anti-inflammatory activity when tested in rats according to the pharmacological test procedures more fully described hereinbelow and are indicated for use as anti-inflammatory agents.

As intermediates in one process for the preparation of the compounds of formula I there are provided compounds having the formula

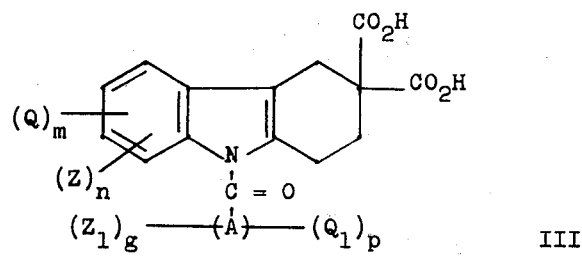

wherein (A) represents phenyl, naphthyl, 2-thienyl, or cyclohexyl; Q and $Q_1$ represent members of the group consisting of lower-alkyl, phenyl-lower-alkyl, lower-alkoxy, phenyl-lower-alkoxy, phenoxy, phenyl, amino, di(lower-alkyl)amino, lower-alkanoylamino, trihalomethyl, trihalomethoxy, halo and hydroxy; Z and $Z_1$ represent members of the group consisting of lower-alkylthio, lower-alkylsulfinyl, lower-alkylsulfonyl and nitro; m represents an integer from 0 to (3-n) inclusive; p represents an integer from 0 to (3-g) inclusive; and n and g represent integers from 0 to 1 inclusive; or $(Q)_m$ taken together with $(Z)_n$, or $(Q_1)_p$ taken together with $(Z_1)_g$ represent methylenedioxy attached to adjacent carbon atoms.

Compounds of formula III where (A) is phenyl or naphthyl are claimed in U.S. Pat. No. 3,687,969.

As intermediate in another process for the preparation of the compounds of formula I there are provided compounds having the formula

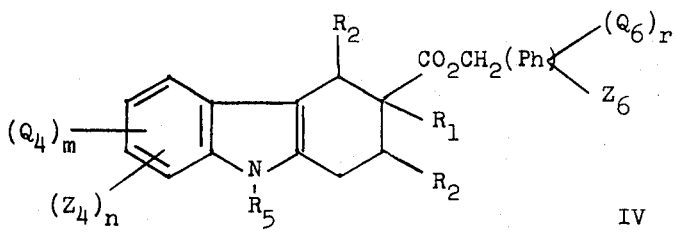

IV wherein $R_5$ represents hydrogen or

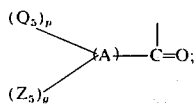

(A) represents phenyl, naphthyl, 2-thienyl, or cyclohexyl; $Q_4$ and $Q_5$ represent substituents selected from lower-alkyl, phenyl-lower-alkyl, lower-alkoxy, phenyl-lower-alkoxy, phenoxy, phenyl, di(lower-alkyl)amino, trihalomethyl, trihalomethoxy and halo, where phenyl is unsubstituted or substituted by from one to three of the same or different substituents selected from lower-alkyl, lower-alkoxy, trihalomethyl and halo; $Z_4$ and $Z_5$ represent lower-alkylthio; $m$ represents an integer from 0 to (3-n) inclusive; $p$ represents an integer from 0 to (3-g) inclusive; $n$ and $g$ represent integers from 0 to 1 inclusive; (Ph) represents phenyl; $Q_6$ represents a substituent selected from lower-alkyl, lower-alkoxy and halo; $r$ represents an integer from 0 to 3 inclusive; $Z_6$ represents hydrogen; and $R_1$ and $R_2$ each represent hydrogen or methyl, at least one of which is hydrogen; or $(Q_4)_m$ taken together with $(Z_4)_n$, or $(Q_5)_p$ taken together with $(Z_5)_g$, or $(Q_6)_r$ taken together with $Z_6$ represent methylenedioxy attached to adjacent carbon atoms.

As intermediates in the preparation of the compound having formula II there are provided compounds having the formula

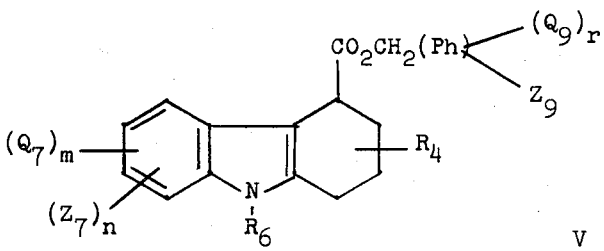

V wherein $R_6$ represents hydrogen or

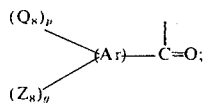

(Ar) represents phenyl or naphthyl; $Q_7$ and $Q_8$ represent substituents selected from lower-alkyl, phenyl-lower-alkyl, lower-alkoxy, phenyl-lower-alkoxy, phenoxy, phenyl, di(lower-alkyl)amino, trihalomethyl, trihalomethoxy and halo, where phenyl is unsubstituted or substituted by from one to three of the same or different substituents selected from lower-alkyl, lower-alkoxy, trihalomethyl and halo; $Z_7$ and $Z_8$ represent lower-alkylthio; $m$ represents an integer from 0 to (3-n) inclusive; $p$ represents an integer from 0 to (3-g) inclusive; $n$ and $g$ represent integers from 0 to 1 inclusive; (Ph) represents phenyl; $Q_9$ represents a substituent selected from lower-alkyl, lower-alkoxy and halo; $r$ represents an integer from 0 to 3 inclusive; $Z_9$ represents hydrogen; and $R_4$ represents hydrogen or methyl; or $(Q_7)_m$ taken together with $(Z_7)_n$, or $(Q_8)_p$ taken together with $(Z_8)_g$, or $(Q_9)_r$ taken together with $Z_9$ represent methylenedioxy attached to adjacent carbon atoms.

The compounds having formula IV and formula V are claimed in copending application Ser. No. 200,205, filed Nov. 18, 1971, now U.S. Pat. No. 3,758,496, issued Sept. 11, 1973.

It will be understood, here and throughout the specification, that when (A) and (Ar) are naphthyl they are 1-naphthyl or 2-naphthyl, and it will be further understood that the substituents represented by Q, $Q_2$, $Q_4$, $Q_7$, Z, $Z_2$, $Z_4$ and $Z_7$; $Q_1$, $Q_3$, $Q_5$, $Q_8$, $Z_1$, $Z_3$, $Z_5$ and $Z_8$; and $Q_6$ and $Q_9$ can occur at any of the available positions of the benzene ring of the tetrahydrocarbazole; the rings represented by (A) and (Ar); and the ring represented by (Ph) respectfully and where, in each case, there is more than one substituent they can occur in any position combination relative to each other, and, in the case of the substituents represented by $Q_1$ to $Q_9$ inclusive, they can be the same or different.

It will also be understood, here and throughout the specification, that when $(Q)_m$ taken together with $(Z)_n$; $(Q_1)_p$ taken together with $(Z_1)_g$; $(Q_2)_m$ taken together with $(Z_2)_n$; $(Q_3)_p$ taken together with $(Z_3)_g$; $(Q_4)_m$ taken together with $(Z_4)_n$:$(Q_5)_p$ taken together with $(Z_5)_g$; $(Q_6)_r$ taken together with $Z_6$; $(Q_7)_m$ taken together with $(Z_7)_n$; $(Q_8)_p$ taken together with $(Z_8)_g$; and $(Q_9)_r$ taken together with $Z_9$ represent methylenedioxy attached to adjacent carbon atoms, each such methylenedioxy group can occur at any of the available adjacent positions of the rings represented by (Ar) and (Ph) to which it is attached, and it will be further understood that for any particular compound of the invention, either or both of $(Q)_m$ taken together with $(Z)_n$ and $(Q_1)_p$ taken together with $(Z_1)_g$ (formulas I and III), or $(Q_2)_m$ taken together with $(Z_2)_n$ and $(Q_3)_p$ taken together with $(Z_3)_g$ (formula II), or one or two or all of $(Q_4)_m$ taken together with $(Z_4)_n$, $(Q_5)_p$ taken together with $(Z_5)_g$, and $(Q_6)_r$ taken together with $Z_6$, (formula IV), or $(Q_7)_m$ taken together with $(Z_7)_n$, $(Q_8)_p$ taken together with $(Z_8)_g$ and $(Q_9)_r$ taken together with $Z_9$ (formula V) can be methylenedioxy attached to adjacent carbon atoms.

As used throughout this specification, the terms lower-alkyl, lower-alkoxy, and lower-alkanoyl mean such groups preferably containing from one to six carbon atoms which can be arranged as straight or branched chains, and, without limiting the generality of the foregoing, are illustrated by methyl, ethyl, propyl, isopropyl, butyl, sec-butyl, amyl, hexyl and the like for alkyl; methoxy, ethoxy, propoxy, isobutoxy, hexyloxy and the like for alkoxy; and acetyl, propionyl, butyryl, isobutyryl, hexanoyl and the like for alkanoyl.

As used throughout this specification the term halo means chloro, bromo, iodo and fluoro.

The free acid forms of the compounds of formulas I and II where R and $R_3$ respectively are hydrogen are convertible to the corresponding salt form by interaction of a particular acid with a base, and such salts are considered to be the full equivalents of the acids and esters of formulas I and II. Examples of such salts are salts of heavy metals such as zinc and iron, alkali metal salts, for example, sodium and potassium; alkali earth metal salts, for example, calcium and barium; the aluminum and magnesium salts; and ammonium salts, such as those derived from ammonia or amines such as methylamine, ethylamine, isopropylamine, hexylamine, dimethylamine, diethylamine, methyl ethylamine, di(-sec-propyl)amine, dihexylamine, methyl cyclohexylamine, pyrrolidine, piperidine, morpholine, choline, glucosamine, 2-hydroxyethylamine, bis(2-hydroxyethyl)amine, tris(2-hydroxyethyl)amine and the like. Of course, by virtue of the herein disclosed pharmaceutical utility of the compounds of formulas I and II the preferred salts are the pharmaceutically acceptable salts and such salts are considered to be the full equivalents, particularly for pharmaceutical use, of the free acids and esters of formulas I and II.

In the process aspects of the invention there are provided the processes described more fully hereinbelow as follows:

The compounds of the invention having formula I are prepared by the methods described and illustrated in the flow charts below.

They are prepared by one method by reacting an appropriate 1-carboxylic acyl-1-phenylhydrazine (formula VI) or the corresponding aldehyde 1-carboxylic acyl-1-phenylhydrazone, e.g., acetaldehyde or benzaldehyde hydrazone, with an appropriate cyclohexanone-4-carboxylic acid or ester thereof (formula VII) or the known cyclohexanone-4,4-dicarboxylic acid (formula VIIa) to give the corresponding 1,2,3,4-tetrahydrocarbazole-3-carboxylic acid or ester thereof (formula I) or corresponding 1,2,3,4-tetrahydrocarbazole-3,3-dicarboxylic acid (formula III) respectively and further reacting the dicarboxylic acid (III), under pyrolytic conditions, in order to effect mono-decarboxylation to give the corresponding compound of formula I (R=H). The condensation reaction is carried out in a suitable solvent, for example acetic acid or, when the corresponding lower-alkyl ester is desired, in an alkanol such as methyl alcohol, ethyl alcohol, isopropyl alcohol or butyl alcohol in the presence of a suitable condensing agent, for example, acids such as hydrochloric, hydrobromic, polyphosphoric, sulfuric and acetic acid, and Lewis acids such as zinc chloride, cuprous chloride, boron trifluoride, boron trifluoride etherate and the like.

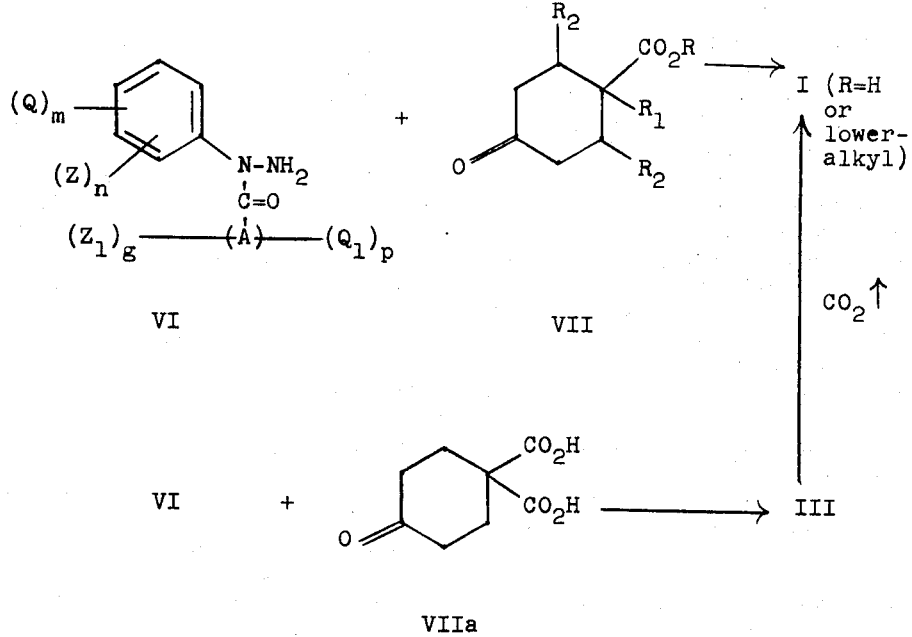

The reaction of the hydrazines, or corresponding acid-addition salt, having formula VI or corresponding aldehyde 1-carboxylic acyl-1-phenylhydrazones with the cyclohexanones having formulas VII and VIIa can be carried out in a suitable solvent at temperatures of from about 20°C. to about 125°C. for from about 15 minutes to several hours, the choice of solvent, catalyst, temperature and time of reaction depending on the nature of the reactants. If an acid-addition salt of the 1-carboxylic acyl-1-phenylhydrazines is employed, an additional condensing agent is not necessary. Generally, the reaction is conveniently carried out by heating a solution of an appropriate 1-carboxylic acyl-1-phenylhydrazine of formula VI in the form of its acid-addition salt, e.g. hydrochloride salt, and an appropriate cyclohexanone of formula VII or VIIIa in glacial acetic acid at about 60° to 70°C. for about 30 minutes. In the case of the aldehyde 1-carboxylic acyl-1-phenylhydrazones, the reaction is conveniently carried out by heating under reflux a solution of the appropriate benzaldehyde or acetaldehyde 1-carboxylic acyl-1-phenylhydrazone and an appropriate cyclohexanone of formula VII (where R=hydrogen or lower-alkyl) or VIIa in glacial acetic acid at from 90°C. to reflux temperature in the presence of an excess of hydrochloric acid or sulfuric acid for 1 to 6 hours; the acid condensing agent can be added initially or subsequent to the heating of the solution of the reactants until liberation of a stoichiometric amount of aldehyde so formed is complete. The monodecarboxylation reaction leading to the compounds of formula I where R is hydrogen can be carried out by heating the appropriate dicarboxylic acid having formula III, if desired in the presence of a suitable solvent, to a temperature where carbon dioxide evolution begins and continuing heating at about that temperature until carbon dioxide evolution ceases. Generally the reaction proceeds readily when an appropriate dicarboxylic acid of formula III is heated, in the absence of solvent, at about 170° to 200°C.

The compounds of the invention having formula I where R is lower-alkyl can also be prepared from the free carboxylic acids (I, R=H) by standard esterification procedures. In view of the sensitivity to hydrolysis of the 9-carboxylic acyl moiety of the compounds having formula I to the strong acidic conditions used in some procedures to effect esterification, for example, treatment with alkanols in the presence of a strong acid, esterification procedures which avoid such conditions are preferred, for example, esterification with diazoalkanes or with alkanols (ROH, where R is lower-alkyl) in the presence of an equivalent of cyclohexylcarbodiimide. Alternatively the free carboxylic acid (I, R=H) can be converted to the acid chloride or bromide, using standard procedures, e.g., reaction with thionyl chloride or bromide, followed by treatment with an appropriate alcohol (ROH, where R is lower-alkyl or 4-acetamidophenyl). The carboxylic acid esters (I, R=alkanoyloxymethyl or unsubstituted or substituted benzoyloxymethyl) are prepared by reacting the free carboxylic acid (I, R=H) with the appropriate chloromethyl akanoate or an appropriate chloromethyl benzoate in a suitable solvent, e.g., dry dimethylformamide, in the presence of a suitable acid acceptor, e.g., sodium or potassium carbonate or sodium or potassium bicarbonate. The chloromethyl alkanoates and benzoates belong to a well-known class of compounds and are readily prepared by a known procedure, i.e., reaction of the corresponding alkanoic acid chlorides or bromides and benzoic acid chlorides or bromides with paraformaldehyde generally in the presence of a small amount of dry zinc chloride.

The intermediate 1-carboxylic acyl-1-phenylhydrazines having formula VI and corresponding aldehyde 1-carboxylic acyl-1-phenylhydrazones used in the preparation of the compounds having formulas I and III are known compounds or are readily prepared by standard procedures from the corresponding phenylhydrazines and corresponding carboxylic acyl halides as follows: To a stirred ice-bath cooled solution of acetaldehyde (or other suitable aldehyde, e.g., benzaldehyde) (1.1 mole) in 300 ml. ether (or other suitable solvent, e.g., methyl alcohol or pyridine) is added slowly the appropriate phenylhydrazine (1 mole) and stirring is continued for 1 hour. The solution is washed with water and the ether layer is separated, dried and evaporated under reduced pressure to give the corresponding acetaldehyde phenylhydrazone which can be purified by standard procedures or used as such in the next step. If pyridine is used as solvent instead of ether, the resulting pyridine solution of the hydrazone is used directly in the next step or is quenched in ice-water and the precipitated hydrazone is collected by filtration. If methyl alcohol is used as solvent, the hydrazone generally precipitates and is collected by filtration. To a stirred ice-bath cooled solution of the thus obtained acetaldehyde phenylhydrazone (0.12 mole) in 80 ml. of pyridine is added slowly the appropriate carboxylic acyl chloride (slight excess over 0.12 mole) and the resulting mixture is allowed to warm to room temperature and diluted with ice-water. The resulting corresponding acetaldehyde 1-carboxylic acyl-1-phenylhydrazone, if a solid, is collected by filtration, washed with water and dried; if a gum or oil, the supernatant liquid is decanted, the residue is dissolved in ether and the solution is washed thoroughly with water, dried and used as such in the next step. Alternatively the acetaldehyde phenylhydrazone is reacted with a slight excess of sodium hydride in dimethylformamide with cooling and the resulting solution of the acetaldehyde phenylhydrazone sodium salt is reacted at room temperature with a slight excess of the appropriate carboxylic acyl chloride for several hours. The mixture is then treated with a sufficient quantity of glacial acetic acid to neutralize excess base and extracted with ether. The ether extract is washed with water, dried, and evaporated to dryness under reduced pressure. The acetaldehyde 1-carboxylic acyl-1-phenylhydrazone so obtained is purified using standard techniques or is used as such in the next step. This latter acylation procedure is preferred when the carboxylic acyl chloride and/or the phenylhydrazone bear an ortho substituent. To a stirred solution or suspension of the thus obtained corresponding acetaldehyde 1-carboxylic acyl-1-phenylhydrazone in ethyl alcohol or in ether is added a solution of hydrogen chloride (in excess of one equivalent) in ether or ethyl alcohol respectively and stirring is continued for 1 hour. If required, additional ether is then added to aid the precipitation of the resulting corresponding 1-carboxylic acyl-1-phenylhydrazine hydrochloride which is collected by filtration and washed with ether and generally is used as such in the next step without further purification. The corresponding free hydrazine can be obtained, if desired, by reaction of the hydrochloride salt with an equivalent amount of appropriate base, using standard procedures.

The phenylhydrazines employed in the preparation of the intermediate compounds having formula VI are known compounds or are readily prepared from the corresponding known anilines, which belong to a well known class of compounds, using standard procedures. For example, a convenient method is the reaction of an appropriately substituted aniline with sodium nitrite in the presence of hydrochloric acid and reduction of the resulting corresponding phenyldiazonium chloride with stannous chloride followed by treatment with sodium hydroxide to give the corresponding substituted phenylhydrazine.

The carboxylic acyl halides employed in the preparation of the intermediate compounds having formula VI are known compounds or are readily prepared from the corresponding known carboxylic acids using standard procedures, e.g., by reaction of an appropriate carboxylic acid with an appropriate halogenating agent such as thionyl chloride or oxalyl chloride.

The intermediate cyclohexanone-4-carboxylic acids having formula VII (R=H) and certain lower-alkyl esters thereof are known compounds. Other lower-alkyl esters thereof can be prepared by standard esterification procedures such as reaction of the carboxylic acid with an appropriate diazoalkane, for example, diazomethane; by reaction of the carboxylic acid with an appropriate alcohol (ROH, where R is lower-alkyl) in the presence of an acid catalyst, for example, sulfuric acid or hydrochloric acid, or in the presence of an equivalent of cyclohexylcarbodiimide; and by reaction of the alkali metal salt of the carboxylic acid with thionyl chloride and further reaction of the acid chloride so formed with an appropriate alchol.

The compounds having formula I are prepared by an alternative method. They are prepared by reacting an appropriate 9-H-1,2,3,4-tetrahydrocarbazole-3-carboxylic acid lower-alkyl ester (formula VIII) or benzyl ester (formula IV, $R_5$=H) with an appropriate carboxylic acyl halide having the formula (IX) below, where X is bromide, chloride or fluoride, to give the corresponding 9-carboxylic acyl-1,2,3,4-tetrahydrocarbazole-3-carboxylic acid lower-alkyl ester (formula I, R = lower-alkyl) or benzyl ester (formula IV,

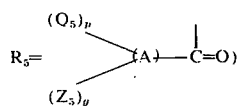

respectively and further subjecting the benzyl ester so obtained to hydrogenolysis to give the corresponding compound of formula I where R is hydrogen.

with an appropriate carboxylic acyl halide (IX), in a suitable solvent, at a temperature ranging from about room temperature to about 100°C. to give the corresponding compound having formula I (R = lower-alkyl) or corresponding compound having formula IV

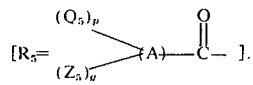

The hydrogenolysis is carried out by subjecting a solution or suspension of the benzyl ester so obtained, in a suitable solvent, to a hydrogen atmosphere at room or elevated temperatures and a pressure of one or more atmospheres in the presence of a suitable catalyst until the required amount of hydrogen has reacted. Suitable solvents that can be used are, for example, methyl alcohol, ethyl alcohol, ethyl acetate or acetic acid and the like. Suitable catalysts that can be used are, for example, nickel, palladium or platinum or such catalysts supported on a suitable medium such as charcoal, e.g., palladium-on-charcoal. The acylation reaction is conveniently carried out by reacting a 9-H-1,2,3,4-tetrahydrocarbazole-3-carboxylic acid lower-alkyl or benzyl ester with an equivalent of sodium hydride in dimethylformamide at about 60° to 100°C. for about 15 minutes and treating a solution of the sodium salt so obtainedd with an equivalent of the carboxylic acyl halide (IX) and continuing hehating at about 60° to 100°C. for about 1 to 2 hours, and isolating the resulting corresponding 9-carboxylic acyl-1,2,3,4-tetrahydrocarbazole-3-carboxylic acid lower-alkyl or benzyl ester by standard procedures. The hydrogenolysis of the benzyl ester so obtained is conveniently carried out by suspending or dissolving it in ethyl alcohol and subjecting it to a hydrogen atmosphere in the presence of five to ten percent palladium-on-charcoal, in the amount of about one to five percent by weight of benzyl ester, at a temperature ranging from room temperature to about 80° C., stopping the reaction when about

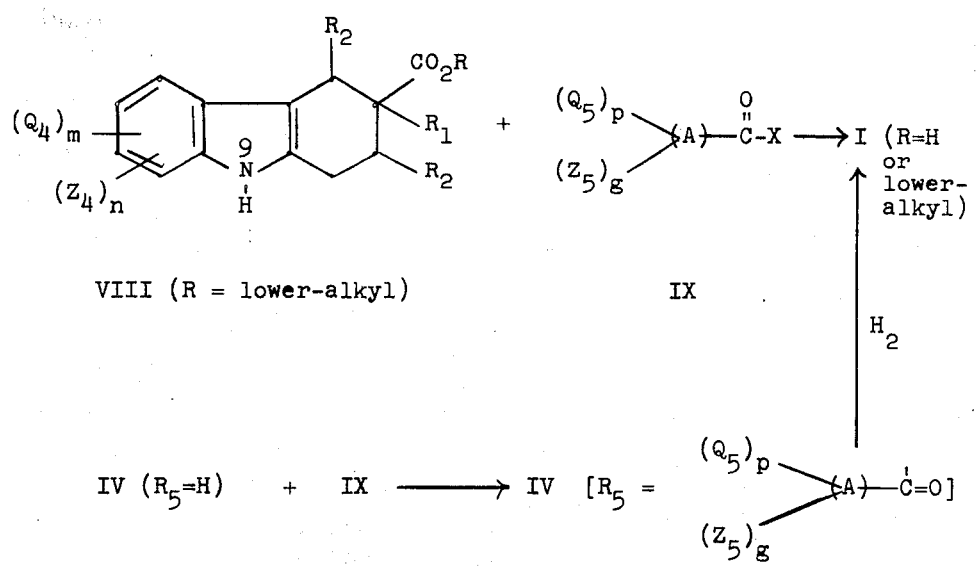

The acylation reaction is carried out by converting an appropriate 9-H-1,2,3,4-tetrahydrocarbazole-3-carboxylic acid ester by known procedures to a suitable salt, for example an alkali metal salt such as the sodium salt (9-Na) and further reacting the salt so obtained the stoichiometric amount of hydrogen has reacted, and isolating and purifying the corresponding 3-carboxylic acid by standard procedures.

The compounds having formula I where R is hydrogen are also prepared by subjecting the corresponding t-butyl ester (I.R = t-butyl) to pyrolytic conditions which selectively remove the t-butyl moiety to give the corresponding free carboxylic acid. The reaction is conveniently carried out by heating a mixture of the t-butyl ester with powdered porous plate in a nitrogen atmosphere at about 210°C.

The carboxylic acyl halides (IX) are known compounds or can be readily prepared from the corresponding carboxylic acids by the known methods described hereinabove.

The intermediate 9-H-1,2,3,4-tetrahydrocarbazole-3-carboxylic acids lower-alkyl esters (VIII, R = lower-alkyl) are prepared by the methods more fully described hereinbelow or are prepared by known esterification procedures from the corresponding 9-H-1,2,3,4-tetrahydrocarbazole-3-carboxylic acids (VIII, R=H). For example, an appropriate carboxylic acid can be treated in an alkanol (ROH, where R is lower-alkyl) in the presence of hydyrogen chloride to give the corresponding ester; or the cyclohexylcarbodiimide method for preparing esters referred to hereinabove may be employed; or an appropriate carboxylic acid can be converted to the alkali metal salt which is then reacted with a halogenating agent to give the corresponding acid halide. The acid halide so obtained is then reacted with an appropriate alcohol (ROH, where R is lower-alkyl or its alkali metal salt to give the corresponding ester. A convenient method is reaction of the carboxylic acid with about an equivalent of sodium hydride to give the corresponding sodium salt and further reaction of the salt with thionyl chloride followed by reaction of the carboxylic acid chloride so obtained with the appropriate alcohol or sodium or potassium salt of the alcohol to give the ester (VIII, R = lower-alkyl). The carboxylic esters can also be prepared by the known procedure of reacting the appropriate carboxylic acid with cyclohexylcarbodiimide to give the corresponding symmetrical carboxylic acid anhydride and treating the anhydride so obtained with an appropriate alcohol in the presence of an acid catalyst, for example zinc chloride. The t-butyl esters, intermediates for the pyrolytic conversion to the compounds of formula I (R=H) as described hereinabove, can be conveniently prepared by this latter procedure.

The 9-H-1,2,3,4-tetrahydrocarbazole-3-carboxylic acid benzyl esters (IV, R₅=H) can be prepared from the corresponding free carboxylic acids and corresponding known benzyl alcohols using the known esterification procedures described hereinabove. Alternatively, they can be prepared by reacting an alkali metal salt of an appropriate carboxylic acid with an appropriate benzyl bromide or chloride in a suitable solvent. The latter reaction is conveniently carried out by reacting the carboxylic acid with an equivalent of a benzyl chloride and an equivalent of sodium carbonate in dimethylformamide at about 80°–100°C. for about one hour. The benzyl bromides and chlorides belong to a group of well known compounds and are generally known or can be prepared from the corresponding known toluenes by standard halogenation procedures, e.g. reaction of an appropriate toluene with sulfuryl chloride or N-bromosuccinimide in the presence of a peroxide such as benzoyl peroxide to give the corresponding toluene-α-chloride or bromide, that is, benzyl chloride or bromide, respectively.

The 9-H-1,2,3,4-tetrahydrocarbazole-3carboxylic acids and their corresponding lower-alkyl esters (VIII) can be prepared from the corresponding phenylhydrazines and cyclohexanone-4-carboxylic acids and its lower-alkyl esters (VII) using the general procedures described hereinabove for the preparation of the tetrahydrocarbazoles having formula I from the corresponding 1-carboxylic acyl-1-phenylhydrazines (VI) and cyclohexanone-4-carboxylic acids (VII).

It will be understood that in the methods described hereinabove for the preparation of the compounds of the invention having formula I that, unless otherwise indicated, (A), Q, Q₁, Z, Z₁, m, n, p, g, R, R₁ and R₂; and (A), (Ph), Q₄, Q₅, Q₆, Z₄, Z₅, Z₆, m, n, p, g, R, R₁, R₂ and R₅ have the same meaning as defined above for formulas I and III; and formula IV, respectively, except where Q and/or Q₁ represents amino or hydroxy. The compounds of the invention having formulas I and III where Q and/or Q₁ each includes one or more hydroxy substituents, and/or Z and/or Z₁ each includes an amino substituent, are prepared, if desired, from the corresponding compounds having formulas I and III where Q and/or Q₁ includes one or more benzyloxy substituents, and/or Z and/or Z₁ includes a nitro substituent, respectively, by well known catalytic hydrogenation procedures whereby said substitutents are converted to hydroxy and/or amino substituents. The hydrogenation is carried out at room temperature in an inert solvent, e.g. ethyl alcohol, under essentially neutral conditions in the presence of a suitable catalyst, e.g. Raney nickel or palladium-on-charcoal, at about atmospheric pressure and the hydrogenation is stopped after the stoichiometric amount of hydrogen has reacted.

The compounds of the invention having formula II are prepared, as illustrated in the flow chart below, from the corresponding 9-H-1,2,3,4-tetrahydrocarbazole-4-carboxylic acid lower-alkyl esters (X, R₃ = lower-alkyl) and benzyl esters (V, R₆=H) using methods similar to those described hereinabove for the preparation of the compounds having formula I from the 9-H-1,2,3,4-tetrahydrocarbazole-3-carboxylic acid alkyl esters (VIII, R = lower-alkyl) and benzyl esters, (IV, R₅=H), that is, by acylation with the an appropriate carboxylic acyl halide having the formula XI below, where X is chloride, bromide or fluoride, and, in the case of the benzyl esters

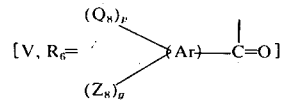

so obtained, subsequent hydrogenolysis, or, in the case of the t-butyl ester (II, R₃=t-butyl), subsequent pyrolysis, to give the corresponding free carboxylic acid (II, R₃=H). Since hydroxy substituents will also undergo acylation during this reaction, compounds of the invention where Q₂ represents hdyroxy are prepared from corresponding compounds where Q₂ is benzyloxy, subsequent to the acylation reaction, as more fully disclosed hereinbelow. The carboxylic acyl halides (XI) are known compounds or can be prepared by known methods described hereinbefore for the preparation of the carboxylic acyl halides of fformula IX.

The compounds of the invention having formula II where R₃ is lower-alkyl, 4-acetamidophenyl, lower-alkanoyloxymethyl, benzoyloxymethyl and benzoyloxymethyl substituted as hereinbefore defined can also be prepared from the free carboxylic acids (II, R₃=H) by standard esterification procedures as described hereinbefore for the preparation of compounds having formula I (R=lower-alkyl, 4-acetamidophenyl, lower-alkanoyloxymethyl, benzoyloxymethyl and benzoyloxymethyl substituted as hereinbefore defined) from the corresponding free carboxylic acids (I, R=H).

acids (X, $R_3$=H) used as intermediates in the preparation of the corresponding lower-alkyl esters (X, $R_3$ = lower-alkyl) and benzyl esters (V, $R_6$=H) are prepared from the corresponding 9-benzyl-1,2,3,4-tetrahy-

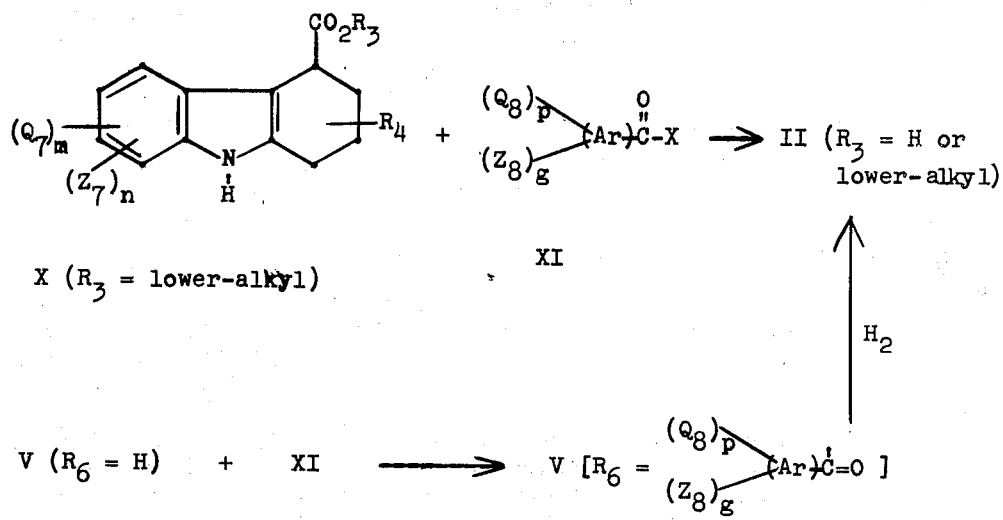

The 9-H-1,2,3,4-tetrahydrocarbazole-4l-carboxylic acid lower-alkyl esters (X, $R_3$ = lower-alkyl) and benzyl esters (V, $R_6$ = H) used as intermediates in the preparation of the compounds having formula II are obtained by reacting the corresponding free 4-carboxylic acids (X, $R_3$ = H) with appropriate known alcohols ($R_3$OH, where $R_3$ is lower-alkyl) or diazoalkanes, and benzyl bromides or chlorides, respectively, using the known esterification procedures described hereinabove for the preparation of the 9-H-1,2,3,4-tetrahydrocarbazole-3-carboxylic acid lower-alkyl esters (VIII, R = lower-alkyl) and benzyl esters (IV, $R_5$=H) respectively; and in the case where $Q_7$ is hydroxy, which substituent is introduced by reductive cleavage of the corresponding compound where $Q_7$ is benzyloxy, as described below, such hydroxy substitutent is concurrently converted to the corresponding compound where $Q_7$ is a benzyloxy substituent, during the preparation of the benzyl ester, or, in the case of the lower-alkyl esters, the hydroxy substituent is converted to a benzyloxy substituent, immediately following the esterification step. The benzyl bromides and chlorides are known compounds or are readily prepared by known halogenating methods from the corresponding toluenes as described hereinabove.

The 9-H-1,2,3,4-tetrahydrocarbazole-4-carboxylic drocarbazole-4-carboxylic acids, having the formula Xa below, by reductive removal of the benzyl moiety using known hydrogenolysis procedures, that is, alkali metal/ammonia chemical reduction, e.g. sodium in liquid ammonia; and in the case where $Q_7$ is a benzyloxy substituent, the benzyl moiety will concurrently undergo reductive removal to give the corresponding compound where $Q_7$ is hydroxy. The 9-benzyl group can be unsubstituted on phenyl or substituted on phenyl, for example, by halo, alkyl, or alkoxy substituents so long as such substitution does not prevent or interfere with the subsequent reductive removal of the 9-benzyl group.

The intermediate 9-benzyl compounds having formula Xa are prepared, as illustrated below, by reaction of at least two equivalents of an appropriate phenylbenzylamine (XII) with one equivalent of an appropriate 6-bromocyclohexanone-2-carboxylic acid methyl or ethyl ester (XIII), in a suitable solvent if desired, to give the corresponding intermediate 6-anilino-cyclohexanone-2-carboxylic acid ester (XIV) which is then heated with a suitable acid catalyst, e.g. zinc chloride, to effect cyclization to the corresponding 9-benzyl-1,2,3,4-tetrahydrocarbazole-4-carboxylic acid ester. The ester so obtained is then hydrolyzed, using standard procedures, to the corresponding free 4-carboxylic acid (Xa).

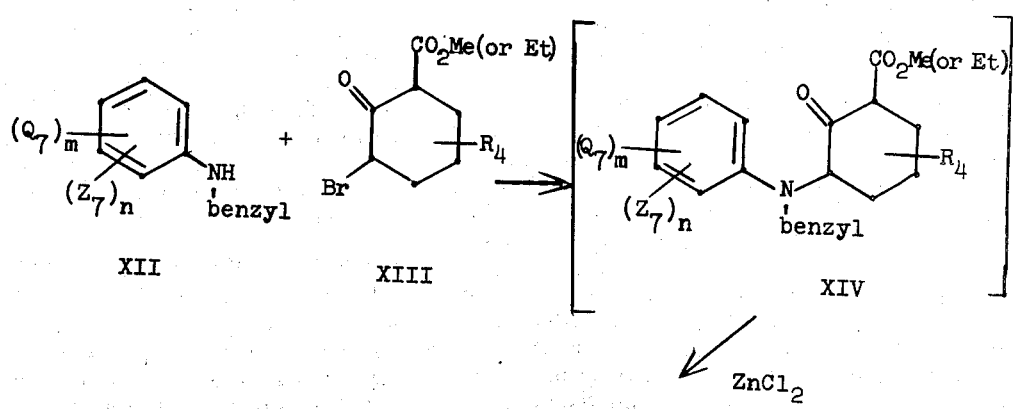

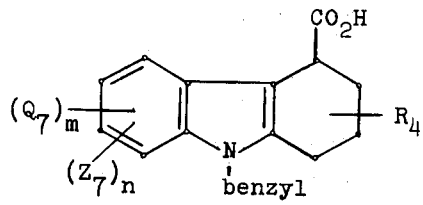

Xa

The reaction is conveniently carried out by mixing together a bromocyclohexanonecarboxylic acid ester (XIII) and two to two and one-half equivalents of a phenylbenzylamine (XII) and allowing the mixture to stand at from about 20°C. to 100°C. for from ½ to 24 hours, depending on the reaction temperature employed, to give the intermediate anilinocyclohexanone (XIV). Depending on the nature of the reactants, the reaction can be performed in the absence of solvent or a suitable solvent such as benzene may be desirable. The intermediate anilinocyclohexanone (XIV) is then heated with zinc chloride at about 100° to 200°C. for about ½ to 2 hours and the corresponding 9-benzyl-1,2,3,4-tetrahydrocarbazole-4-carboxylic acid ester so obtained is treated with potassium hydroxide in aqueous ethyl or methyl alcohol to give the free carboxylic acid (Xa).

The 6-bromocyclohexanone-2-carboxylic acid esters (XIII) used as intermediates in the above described procedure are known compounds or can be readily prepared by reacting the corresponding known cyclohexanone-2-carboxylic acid esters with bromine in a suitable solvent. The reaction is conveniently carried out by treating a cooled solution of the appropriate cyclohexanone-2-carboxylic acid ester in ether or carbon tetrachloride with an equivalent or slight excess of bromine, allowing the solution to stand at room temperature for about one hour, and isolating the resulting 6-bromocyclohexanone-2-carboxylic acid ester by standard techniques.

The intermediate phenylbenzylamines (XII) are known compounds or are readily prepared by standard procedures from the corresponding known anilines and corresponding known benzaldehydes as follows: To a stirred warm solution of an appropriate anailine (1.0 mole) in 400 ml. dry methyl alcohol is added dropwise an appropriate benzaldehyde and the solution is heated at reflux for thirty minutes and then cooled on ice. The resulting Schiff base is collected by filtration and washed with methyl alcohol. To a suspension of the latter in methyl alcohol is added portionwise, sodium borohydride (1.0 mole) and the mixture is refluxed about 15 to 30 minutes after completion of the addition. Water (200 ml.) is added and the mixture is extracted with ether and the ether extract is dried and evaporated to dryness to give the corresponding phenylbenzylamine which is used as such in the next step, or, if desired, is purified by standard procedures before use.

It will be understood that in the methods described hereinabove for the preparation of the compounds of the invention having formula II that, unless otherwise indicated, (Ar), (Ph), $Q_7$, $Q_8$, $Q_9$, $Z_7$, $Z_8$, $Z_9$, $m$, $n$, $p$, $g$, $r$, $R_3$, $R_4$ and $R_6$ have the same meaning as defined above for formulas II and V respectively. The compounds of the invention having formula II where $Q_2$ and/or $Q_3$ each includes one or more hydroxy substituents are prepared, if desired, from the corresponding compounds having formula V where $Q_7$ and/or $Q_8$ respectively, includes one or more benzyloxy substituents, by known catalytic hydrogenation procedures as described hereinabove for the preparation of compounds of formula I where Q and/or $Q_1$ includes one or more hydroxy substituents.

The antiinflammatory activity of the compounds of formulas I and II was determined by their ability to inhibit in rats one or more of the following: asbestos pellet-induced granuloma weight increase; carrageenin-induced foot edema; and adjuvant-induced arthritis. The following are brief descriptions of the pharmacological test procedures employed:

Asbestos Pellet Granuloma Test in Rats

Young male rats weighing 100–120 g. are used. Under light ether anesthesia, a single sterilized asbestos pellet weighing approximately 30 mg. is implanted subcutaneously in the interscapular area via a small skin incision and closed with a wound clip. In any other assay, the pellet weights are within a 2 mg. range. Beginning on the day of pellet implantation, the animals receive 7 daily medications of test compound suspended by triturating in 1% gum tragacanth using a ground glass homogenizer and administered by gavage in a volume of 1 ml/100 g body weight. Control animals receive the vehicle only. Food and water are permitted ad libitum. Twenty-four hours after the last medication, the animals are weighed, sacrificed and the pellets with surrounding granuloma carefully removed and weighed.

Inhibition of Carrageenin-Induced Foot Edema in Rats

Young male rats weighing 100–110 g are used. Food is withdrawn approximately 18 hours prior to medication but the animals are permitted free access to drinking water up to the time of medication. Drugs to be tested are suspended by triturating in 1% gum tragacanth using ground glass homogenizers and administered by gavage in a volume of 1 ml/100 g body weight.

Control animals receive the gum tragacanth only. One hour after medication, 0.05 ml of 1% suspension of carrageenin in 0.9% saline is injected into the plantar tissue of the left hind paw. Three hours after injection of the carrageenin, edema formation, i.e., increase in foot volume (difference between left hind paw and the uninjected right hind paw) is measured plethysmographically in the unanesthetized rat.

Inhibition Adjuvant-Induced Arthritis in Rats

Adult male rats weighing 200-230 grams are used. Adjuvant (M. butyricum), 0.1 ml of a 0.6% suspension in heavy mineral oil, is injected into the plantar tissue of the left hind paw. A negative control group is injected with mineral oil only. Beginning on the ninth day after adjuvant injection (polyarthritis does not appear until approximately the tenth day after adjuvant administration), the animals receive 6 daily medications of test compound suspended by triturating in 1% gum tragacanth using a ground glass homogenizer and administered by gavage in a volume of 1 ml/100 g body weight. Both the negative control and adjuvant injected control animals receive the vehicle only. Food and water are permitted ad libitum. Twenty-four hours after the last medication, the animals are weighed, the degree of arthritic involvement, i.e., increase in foot volume and plasma inflammation units are determined. Foot volume is measured plethysmographically in the unanesthetized rat.

The compounds of the invention having formulas I and II were found to be effective as antiinflammatory agents when administered to rats, as disclosed hereinabove, in the amounts of 40 to 160 mg per kilogram of body weight per dosage unit depending upon the compound used and the condition to be treated. The actual determination of the numerical biological data definitive for a particular compound is readily determined by standard test procedures by technicians having ordinary skill in pharmacological test procedures, without the need for any extensive experimentation.

The compounds having formulas I and II and their pharmaceutically acceptable salts can be prepared for use by conventional pharmaceutical procedures; that is, they can be incorporated in unit dosage form in tablets or capsules for oral administration either alone or in combination with suitable adjuvants such as calcium carbonate, starch, lactose, talc, magnesium stearate, gum acacia, and the like; or as aqueous or oil suspensions or solutions in a pharmaceutically acceptable vehicle such as aqueous alcohol, glycol, oil solutions or oil water emulsions for oral or parenteral administration.

The molecular structures of the compounds of this invention were assigned on the basis of the method of their synthesis and study of their infrared, and in some cases, nuclear magnetic resonance (NMR) spectra, and confirmed by the correspondence between calculated and found values for the elementary analysis for representative examples.

The invention is illustrated by the following examples without, however, being limited thereto.

EXAMPLE 1

A. 9-Benzoyl-1,2,3,4-tetrahydrocarbazole-3-carboxylic acid

9-Benzoyl-1,2,3,4-tetrahydrocarbazole-3,3-dicarboxylic acid (3.7 g.) was heated at 170°-200°C., till carbon dioxide evolution ceased, to give 2.5 g. of the title compound; m.p. 188°-190°C. (benzene).

A-1.
9-Benzoyl-1,2,3,4-tetrahydrocarbazole-3-carboxylic acid (alternative preparation)

A suspension of 30 g. of benzaldehyde 1188°-1-phenylhydrazone (m.p. 112°-114°C.) and 14.2 g. of cyclohexanone4-carboxylic acid in 100 ml. glacial acetic acid containing 5 g. of concentrated sulfuric acid was heated on a steambath at about 95°C. for 3 ½ hours. The mixture was poured into one liter of ice-cold water with stirring. The water was decanted from the resulting gummy residue which was then crystallized from ethyl acetate and recrystallized from ethyl alcohol to give 17 g. of the title compound; m.p. 118°-192°C.

B.
9-Benzoyl-1,2,3,4-tetrahydrocarbazole-3,3-dicarboxylic acid

1-Benzoyl-1-phenylhydrazine hydrochloride (5 g.) and 4 g. of cyclohexanone-4,4-dicarboxylic acid in 10 ml. of glacial acetic acid were heated at 60°-70°C. for thirty minutes. The mixture was diluted with water and the resulting solid was collected by filtration and washed with water to give 7.1 g. of the title compound; m.p. 160°C. (acetone and hexane).

EXAMPLE 2

A.
9-(4-Chlorobenzoyl)-1,2,3,4-tetrahydrocarbazole-3-carboxylic acid

Following a procedure similar to that of Example 1A but using 3.7 g. of 9-(4-chlorobenzoyl)-1,2,3,4-tetrahydrocarbazole-3,3-dicarboxylic acid there was obtained 2.5 g. of the title compound; m.p. 210°-211°C. (benzene-hexane).

B.
9-(4-Chlorobenzoyl)-1,2,3,4-tetrahydrocarbazole-3,3-dicarboxylic acid

Following a procedure similar to that of Example 1B but using 10.7 g. of 1-(4-chlorobenzoyl)-1-phenylhydrazine hydrochloride and 13 g. of cyclohexanone-4,4-dicarboxylic acid there was obtained crude product, a solution of which in ether was extracted with potassium bicarbonate solution. Acidification of the bicarbonate extract with 10% hydrochloric acid and collection of the resulting solid by filtration yielded 2.7 g. of the title compound; m.p. 210°-212°C. (ethyl acetate-benzene).

EXAMPLE 3

A.
9-Benzoyl-6,7-dimethoxy-1,2,3,4-tetrahydrocarbazole-3-carboxylic acid

Following a procedure similar to that of Example 1A but using 5 g. of 9-benzoyl-6,7-dimethoxy-1,2,3,4-tetrahydrocarbazole-3,3-dicarboxylic acid there was obtained 2.5 g. of the title compound; m.p. 191°-194°C. (benzene-hexane).

B.
9-Benzoyl-6,7-dimethoxy-1,2,3,4-tetrahydrocarbazole-3,3-dicarboxylic acid

Following a procedure similar to that of Example 1B but using 9.3 g. of 1-benzoyl-1-(3,4-dimethoxyphenyl)hydrazine hydrochloride (m.p. 150°-156°C.) and 6 g.

of cyclohexanone-4,4-dicarboxylic acid there was obtained 8 g. crude title compound used directly in the next step; m.p. of purified title compound, 222°C. dec. (benzene).

EXAMPLE 4

A.

9-(4-Toluoyl)-1,2,3,4-tetrahydrocarbazole-3-carboxylic acid

Following a procedure similar to that of Example 1A but using 5 g. of 9-(4-toluoyl)-1,2,3,4-tetrahydrocarbazole-3,3-dicarboxylic acid there was obtained 3 g. of the title compound; m.p. 210°–212°C. (acetone-hexane).

B.

9-(4-Toluoyl)-1,2,3,4-tetrahydrocarbazole-3,3-dicarboxylic acid

Following a procedure similar to that of Example 1B but using 5.4 g. of 1-(4-toluoyl)-1-phenylhydrazine hydrochloride (m.p. 170°–176°C.) and 4.5 g. of cyclohexanone-4,4-dicarboxylic acid there was obtained 7.2 g. of the title compound; m.p. 190°–195°C.

EXAMPLE 5

A.

9-(4-Fluorobenzoyl)-1,2,3,4-tetrahydrocarbazole-3-carboxylic acid

Following a procedure similar to that of Example 1A but using 4.3 g. of 9-(4-fluorobenzoyl)-1,2,3,4-tetrahydrocarbazole-3,3-dicarboxylic acid there was obtained 3.2 g. of the title compound; m.p. 180°–182°C. (acetone-hexane).

B. 9-(4-Fluorobenzoyl)-1,2,3,4-tetrahydrocarbazole-3,3-dicarboxylic acid

Following a procedure similar to that of Example 1B but using 5.8 g. of 1-(4-fluorobenzoyl)-1-phenylhydrazine hydrochloride (m.p. 173°–177°C.) and 4.5 g. cyclohexanone-4,4-dicarboxylic acid there was obtained 7 g. of the title compound; m.p. 190°–195°C.

EXAMPLE 6

A.

9-(4-Anisoyl)-1,2,3,4-tetrahydrocarbazole-3-carboxylic acid

Following a procedure similar to that of Example 1A but using 5.6 g. of 9-(4-anisoyl)-1,2,3,4-tetrahydrocarbazole3,3-dicarboxylic acid there was obtained 3.3 g. of the title compound; m.p. 195°C.

B.

9-(4-Anisoyl)-1,2,3,4-tetrahydrocarbazole-3,3-dicarboxylic acid

Following a procedure similar to that of Example 1B but using 4.6 g. of 1-(4-anisoyl)-1-phenylhydrazine hydrochloride (m.p. 168°–170°C.) and 3.6 g. of cyclohexanone-4,4-dicarboxylic acid there was obtained 3.3 g. of the title compound; m.p. 205°–207°C. (benzene-hexane).

EXAMPLE 7

A.

9-(3,4,5-Trimethoxybenzoyl)-1,2,3,4-tetrahydrocarbazole-3-carboxylic acid

Following a procedure similar to that of Example 1A but using the 9-(3,4,5-trimethoxybenzoyl)-1,2,3,4-tetrahydrocarbazole-3,3-dicarboxylic acid obtained in 7B below there was obtained 5 g. of the title compound: m.p. 234°–236°C.

B.

9-(3,4,5-Trimethoxybenzoyl)-1,2,3,4-tetrahydrocarbazole-3,3-dicarboxylic acid Following a procedure similar to that of Example 1B but using 5.4 g. of 1-(3,4,5-trimethoxybenzoyl)-1-phenylhydrazine hydrochloride and 3.6 g. of cyclohexanone-4,4-dicarboxylic acid there was obtained the title compound; m.p. 208°C.

EXAMPLE 8

A.

9-(3-Toluoyl)-1,2,3,4-tetrahydrocarbazole-3-carboxylic acid

Following a procedure similar to that of Example 1A but using 4.3 g. of 9-(3-toluoyl)-1,2,3,4-tetrahydrocarbazole3,3-dicarboxylic acid there was obtained 3.2 g. of the title compound; m.p. 180°–182°C.

B.

9-(3-Toluoyl)-1,2,3,4-tetrahydrocarbazole-3,3-dicarboxylic acid

Following a procedure similar to that of Example 1B but using 5.6 g. of 1-(3-toluoyl)-1-phenylhydrazine hydrochloride (m.p. 170°–172°C.) and 4.5 g. of cyclohexanone-4,4-dicarboxylic acid there was obtained 6.6 g. of the title compound; m.p. 195°–200°C.

EXAMPLE 9

9-Benzoyl-6-methyl-1,2,3,4-tetrahydrocarbazole-3-carboxylic acid

Following a procedure similar to that of Example 1B but using 10.6 g. of 1-benzoyl-1-(4-tolyl) hydrazine hydrochloride (m.p. 155°C. dec.) and 6.5 g. of cyclohexanone-4-carboxylic acid there was obtained 9.6 g. of the title compound; m.p. 200°–202°C. (acetone-water).

EXAMPLE 10

9-(4-Fluorobenzoyl)-6-methyl-1,2,3,4-tetrahydrocarbazole-3-carboxylic acid

Following a procedure similar to that of Example 1B but using 15.6 g. of 1-(4-fluorobenzoyl)-1-(4-tolyl) hydrazine hydrochloride (m.p. 155°C. dec.) and 8.4 g. of cyclohexanone-4-carboxylic acid there was obtained 12.7 g. of the title compound; m.p. 230°–233°C. (acetone-water).

EXAMPLE 11

9-[3-(Trifluoromethyl)benzoyl]-1,2,3,4-tetrahydrocarbazole-3-carboxylic acid Following a procedure similar to that of Example 1B but using 10 g. of 1-[3-(trifluoromethyl)benzoyl]-1-phenylhydrazine hydrochloride and 5.73 g. of cyclohexanone-4-carboxylic acid there was obtained 8.8 g. of the title compound; m.p. 173°–175°C. (ether-hexane).

EXAMPLE 12

9-(4-t-Butylbenzoyl)-1,2,3,4-tetrahydrocarbazole-3-carboxylic acid

Following a procedure similar to that of Example 1B but using 19 g. of 1-(4-t-butylbenzoyl)-1-phenylhydrazine hydrochloride and 10.7 g. of cyclohexanone-4-carboxylic acid there was obtained 13.7 g. of the title compound; m.p. 174°–175°C. (acetone-water).

EXAMPLE 13

9-(3-Bromobenzoyl)-1,2,3,4-tetrahydrocarbazole-3-carboxylic acid

Following a procedure similar to that of Example 1B but using 10.7 g. of 1-(3-bromobenzoyl)-1-phenylhydrazine hydrochloride and 5.35 g. of cyclohexanone-4-carboxylic acid there was obtained 10.2 g. of the title compound; m.p. 185°–186°C. (acetone-water),

EXAMPLE 14

9-Benzoyl-6-fluoro-1,2,3,4-tetrahydrocarbazole-3-carboxylic acid

Following a procedure similar to that of Example 1B but using 11 g. of 1-benzoyl-1-(4-fluorophenyl) hydrazine hydrochloride and 6.87 g. of cyclohexanone-4-carboxylic acid there was obtained 10.5 g. of the title compound; m.p. 218°–220°C. (acetone-water),

EXAMPLE 15

9-(4-Toluoyl)-6-methyl-1,2,3,4-tetrahydrocarbazole-3-carboxylic acid

Following a procedure similar to that of Example 1B but using 3.8 g. of 1-(4-toluoyl)-1-(4-tolyl) hydrazine hydrochloride (m.p. 273°–275°C.) and 2.22 g. of cyclohexanone-4-carboxylic acid there was obtained 3 g. of the title compound; m.p. 200°–203°C. (isopropyl alcohol).

EXAMPLE 16

9-(4-Toluoyl)-6-fluoro-1,2,3,4-tetrahydrocarbazole-3-carboxylic acid

Following a procedure similar to that of Example 1B but using 10 g. of 1-(4-toluoyl)-1-(4-fluorophenyl) hydrazine hydrochloride and 5.23 g. of cyclochexanone-4-carboxylic acid there was obtained 9.7 g. of the title compound; m.p. 229°–231°C. (acetone-water).

EXAMPLE 17

9-(4-Fluorobenzoyl)-6-fluoro-1,2,3,4-tetrahydrocarbazole-3carboxylic acid

Following a procedure similar to that of Example 1B but using 12.2 g. of 1-(4-fluorobenzoyl)-1-(4-fluorophenyl) hydrazine hydrochloride (m.p. 175°C. dec.) and 6.5 g. of cyclohexanone-4-carboxylic acid there was obtained 12.2 g. of the title compound; m.p. 195°–196°C. (acetone-water).

EXAMPLE 18

9-(4-Anisoyl)-6-methyl-1,2,3,4-tetrahydrocarbazole-3-carboxylic acid

Following a procedure similar to that of Example 1B but using 3.3 g. of 1-(4-anisoyl)-1-(4-tolyl) hydrazine hydrochloride (m.p. 149°–153°C.) and 1.91 g. of cyclohexanone-4-carboxylic acid there was obtained 5.1 g. of the title compound; m.p. 172°–173°C. (isopropyl alcohol).

EXAMPLE 19

9-(4-Anisoyl)-6-fluoro-1,2,3,4-tetrahydrocarbazole-3-carboxylic acid

Following a procedure similar to that of Example 1B but using 14 g. of 1-(4-anisoyl)-1-(4-fluorophenyl) hydrazine hydrochloride and 7.03 g. of cyclohexanone-4-carboxylic acid there was obtained 13.5 g. of the title compound; m.p. 197°–198°C. (acetone-water).

EXAMPLE 20

9-(4-Chlorobenzoyl)-6-methoxy-1,2,3,4-tetrahydrocarbazole-3carboxylic acid

Following a procedure similar to that of Example 1B but using 11 g. of 1-(4-chlorobenzoyl)-1-(4-methoxyphenyl) hydrazine hydrochloride and 6.2 g. of cyclohexanone-4-carboxylic acid there was obtained 3.2 g. of the title compound; m.p. 269°–273°C. (tetrahydrofuran-ether).

EXAMPLE 21

9-Benzoyl-6-methoxy-1,2,3,4-tetrahydrocarbazole-3-carboxylic acid

Following a procedure similar to that of Example 1B but using 8.9 g. of 1-benzoyl-1-(4-methoxyphenyl) hydrazine hydrochloride and 4.97 g. of cyclohexanone-4-carboxylic acid there was obtained 8.9 g. of the title compound; m.p. 216°–219°C. (acetone-water).

9-Benzoyl-6-methoxy-1,2,3,4-tetrahydrocarbazole-3-carboxylic acid (alternative preparation)

A solution of 75 g. of benzaldehyde 1-benzoyl-1-(4-methoxyphenyl)hydrazone and 42.6 g. of cyclohexanone-4-carboxylic acid in one liter of acetic acid saturated with hydrogen chloride was heated under reflux for three hours during which time hydrogen chloride was continually passed through the solution. The solution was poured into four liters of ice-water and the resulting solid was collected by filtration to give 47.4 g. of the title compound; m.p. 218°–220°C. (methyl alcohol).

The benzaldehyde 1-benzoyl-1-(4-methoxyphenyl) hydrazone was prepared as follows: To a solution of 69 g. of 4-methoxyphenylhydrazine in one liter of methyl alcohol was added 53 g. of benzaldehyde and the mixture was heated under reflux for one-half hour. The mixture was cooled to 0°C., filtered, and the benzaldehyde 4-methoxyphenylhydrazone (m.p. 126°–129°C.) was dissolved in 450 ml. pyridine and 63 g. of benzoyl chloride was then added during five minutes with stirring and water bath cooling. After one-half hour the reaction mixture was poured into 2 liters of ice-water and the solids were collected by filtration to give 119 g. of benzaldehyde -benzoyl-1-(4-methoxyphenyl)hydrazone; m.p. 151°–153°C. (isopropyl alcohol).

9-Benzoyl-6-methoxy-1,2,3,4-tetrahydrocarbazole-3-carboxylic acid when administered to rats at 100 mg per kilogram of body weight per dosage unit resulted in 10.7 percent inhibition of asbestos pellet-induced granuloma weight increase and 40 percent inhibition of carrageenin-induced foot edema. This compound did not exhibit inhibition of adjuvant-induced arthritis when administered to rats at 100 mg per kilogram of body weight per dosage unit.

This compound also was found to exhibit antipyretic activity when administered orally to rats at 100 mg per kilogram of body weight in a standad pharmacological test procedure and is indicated for use as an antipyretic agent. Antiypretic activity was determined in a test procedure in which fever is produced in rats by the subcutaneous injection of 10% Brewer's yeast suspension in saline; the test drug suspended in gum tragacanth then is administered orally to the fevered rats to determine its ability to reduce fever.

EXAMPLE 22

9-(4-Chlorobenzoyl)-6-methyl-1,2,3,4-tetrahydrocarbazole-3-carboxylic acid

Following a procedure similar to that of Example 1B but using 16.5 g. of 1-(4-chlorobenzoyl)-1-(4-tolyl)hydrazine hydrochloride and 9.93 g. of cyclohexanone-4-carboxylic acid there was obtained 8.9 g. of the title compound; m.p. 211°–214°C. (isopropyl alcohol).

EXAMPLE 23

9-(4-Fluorobenzoyl)-6-methoxy-1,2,3,4-tetrahydrocarbazole-3-carboxylic acid

Following a procedure similar to that of Example 1B but using 6.3 g. 1-(4-fluorobenzoyl)-1-(4-methoxyphenyl) hydrazine hydrochloride and 2.98 g. of cyclohexanone-4-carboxylic acid there was obtained 3.7 g. of the title compound; m.p. 258°–260°C. (acetone-water).

EXAMPLE 24

9-(4-Toluoyl)-6-methoxy-1,2,3,4,-tetrahydrocarbazole-3-carboxylic acid

Following a procedure similar to that of Example 1B but using 5.6 g. of 1-(4-toluoyl)-1-(4-methoxyphenyl) hydrazine hydrochloride and 3.7 g. of cyclohexanone-4-carboxylic acid there was obtained 7 g. of the title compound; m.p. 257°–258°C.

EXAMPLE 25

9-(3-Anisoyl)-1,2,3,4-tetrahydrocarbazole-3-carboxylic acid

Following a procedure similar to that of Example 1B but using 11 g. of 1-(3-anisoyl)-1-phenylhydrazine hydrochloride and 6.1 g. of cyclohexanone-4-carboxylic acid there was obtained 11.2 g. of the title compound; m.p. 197°–200°C. (acetone-water).

EXAMPLE 26

9-(4-Ethoxybenzoyl)-1,2,3,4,-tetrahydrocarbazole-3-carboxylic acid

Following a procedure similar to that of Example 1B but using 9 g. of 1-(4-ethoxybenzoyl)-1-phenylhydrazine hydrochloride and 5 g. of cyclohexanone-4-carboxylic acid there was obtained 5.2 g. of the title compound; m.p. 179°–182°C. (acetone-water).

EXAMPLE 27

9-(3,4-Methylenedioxybenzoyl)-1,2,3,4-tetrahydrocarbazole-3-carboxylic acid

Following a procedure similar to that of Example 1B but using 13.6 g. of 1-(3,4-methylenedioxybenzoyl)-1-phenylhydrazine hydrochloride (m.p. 175°–185°C.) and 6.64 g. of cyclohexanone-4-carboxylic acid there was obtained 13.4 g. of the title compound; m.p. 198°–200°C. (acetone-water).

EXAMPLE 28

9-(3-Chlorobenzoyl)-1,2,3,4-tetrahydrocarbazole-3-carboxylic acid

Following a procedure similar to that of Example 1B but using 11.2 g. of 1-(3-chlorobenzoyl)-1-phenylhydrazine hydrochloride and 6.12 g. of cyclohexanone-4-carboxylic acid there was obtained 11.5 g. of the title compound; m.p. 179°–181°C. (ether-hexane).

EXAMPLE 29

9-(3-Iodobenzoyl)-1,2,3,4-tetrahydrocarbazole-3-carboxylic acid

Following a procedure similar to that of Example 1B but using 21.7 g. of 1-(3-iodobenzoyl)-1-phenylhydrazine hydrochloride and 0.5 g. of cyclohexanone-4-carboxylic acid there was obtained 11.5 g. of the title compound; m.p. 210°–212°C. (acetone-water).

EXAMPLE 30

9-Benzoyl-6-benzyloxy-1,2,3,4-tetrahydrocarbazole-3-carboxylic acid

Following a procedure similar to that of Example 1B but using 15.5 g. of 1-benzoyl-1-(4-benzyloxyphenyl)-hydrazine hydrochloride and 6.4 g. cyclohexanone-4-carboxylic acid there was obtained 16.3 g. of the title compound; m.p. 193°–194°C. (acetone-water).

Alternatively the 9-benzoyl-1,2,3,4-tetrahydrocarbazole-3-carboxylic acids above (Examples 9 to 30 inclusive) can be prepared following a procedure similar to that of Example 1A but substituting for 9-benzoyl-1,2,3,4-tetrahydrocarbazole-3,3-dicarboxylic acid an equivalent amount of the following:

a-1. 9-benzoyl-6-methyl-1,2,3,4-tetrahydrocarbazole-3,3-dicarboxylic acid;
a-2. 9-(4-fluorobenzoyl)-6-methyl-1,2,3,4-tetrahydrocarbazole-3,3-dicarboxylic acid;
a-3. 9-[3-(trifluoromethyl)benzoyl]-1,2,3,4-tetrahydrocarbazole-3,3-dicarboxylic acid;
a-4. 9-(4-t-butylbenzoyl)-1,2,3,4-tetrahydrocarbazole-3,3-dicarboxylic acid;
a-5. 9-(3-bromobenzoyl)-1,2,3,4-tetrahydrocarbazole-3,3-dicarboxylic acid;
a-6. 9-benzoyl-6-fluoro-1,2,3,4-tetrahydrocarbazole-3,3,-dicarboxylic acid;
a-7. 9-(4-toluoyl)-6-methyl-1,2,3,4-tetrahydrocarbazole-3,3-dicarboxylic acid;
a-8. 9-(4-toluoyl)-6-fluoro-1,2,3,4-tetrahydrocarbazole-3,3-dicarboxylic acid;
a-9. 9-(4-fluorobenzoyl)-6-fluoro-1,2,3,4-tetrahydrocarbazole-3,3-dicarboxylic acid;
a-10. 9-(4-anisoyl)-6-methyl-1,2,3,4-tetrahydrocarbazole-3,3-dicarboxylic acid;
a-11. 9-(4-anisoyl)-6-fluoro-1,2,3,4-tetrahydrocarbazole-3,3-dicarboxylic acid;
a-12. 9-(4-chlorobenzoyl)-6-methoxy-1,2,3,4-tetrahydrocarbazole-3,3-dicarboxylic acid;
a-13. 9-benzoyl-6-methoxy-1,2,3,4-tetrahydrocarbazole-3,3-dicarboxylic acid;
a-14. 9-(4-chlorobenzoyl)-6-methyl-1,2,3,4-tetrahydrocarbazole-3,3-dicarboxylic acid;
a-15. 9-(4-fluorobenzoyl)-6-methoxy-1,2,3,4-tetrahydrocarbazole-3,3-dicarboxylic acid;
a-16. 9-(4-toluoyl)-6-methoxy-1,2,3,4-tetrahydrocarbazole-3,3-dicarboxylic acid;
a-17. 9-(3-anisoyl)-1,2,3,4-tetrahydrocarbazole-3,3-dicarboxylic acid;
a-18. 9-(4-ethoxybenzoyl)-1,2,3,4-tetrahydrocarbazole-3,3-dicarboxylic acid;
a-19. 9-(3,4-methylenedioxybenzoyl)-1,2,3,4-tetrahydrocarbazole-3,3-dicarboxylic acid;
a-20. 9-(3-chlorobenzoyl)-1,2,3,4-tetrahydrocarbazole-3,3-dicarboxylic acid;
a-21. 9-(3-iodobenzoyl)-1,2,3,4-tetrahydrocarbazole-3,3-dicarboxylic acid; and a-22. 9-benzoyl-6-benzyloxy-1,2,3,4-tetrahydrocarbazole-3,3-dicarboxylic acid.

The intermediate 9-benzoyl-1,2,3,4-tetrahydrocarbazole-3,3-dicarboxylic acids above (a-1 to a-22) can be obtained by substituting for cyclohexanone-4-carboxylic acid in Examples 9 to 30 inclusive, equivalent amounts of cyclohexanone-4,4-dicarboxylic acid.

EXAMPLE 31

Ethyl 9-(4-toluoyl)-1,2,3,4-tetrahydrocarbazole-3-carboxylate 1-(4-Toluoyl)-1-phenylhydrazine hydrochloride (13 g.) and 8.7 g. of ethyl cyclohexanone-4-carboxylate (prepared in situ from the corresponding ethylene ketal) in 40 ml. glacial acetic acid, and 5 ml. glacial acetic acid saturated with hydrogen chloride was warmed on a steam bath for thirty minutes, diluted with water and extracted with ether. The ether extracts were washed with potassium bicarbonate solution and water, dried, and evaporated to dryness. The residue was chromatographed on silica gel using 10% ether-pentane as eluant to give 12.7 g. of the title compound; m.p. 70°–72°C. (hexane-ether).

EXAMPLE 32

Ethyl 9-benzoyl-1,2,3,4-tetrahydrocarbazole-3-carboxylate

Following a procedure similar to that of Example 31 and using 11 g. of 1-benzoyl-1-phenylhydrazine hydrochloride and 7.62 g. of ethyl cyclohexanone-4-carboxylate (prepared in situ from the corresponding ethylene ketal) there was obtained 6.2 g. of the title compound; m.p. 67°–69°C. (ether-pentane).

EXAMPLE 33

9-Benzoyl-2,4-dimethyl-1,2,3,4-tetrahydrocarbazole-3-carboxylic acid

Following a procedure similar to that of Example 1B but using 6.5 g. of 1-benzoyl-1-phenylhydrazine hydrochloride and 4.6 g. 3,5-dimethylcyclohexanone-4-carboxylic acid and dissolving the resulting solid so obtained in five percent potassium bicarbonate solution followed by reprecipitation with dilute hydrochloric acid there was obtained 4.2 g. of the title compound; m.p. 142°–145°C. (ether-hexane).

EXAMPLE 34

A. 9-Benzoyl-1,2,3,4-tetrahydrocarbazole-4-carboxylic acid

A solution of 5.6 g. benzyl 9-benzoyl-1,2,3,4-tetrahydrocarbazole-4-carboxylate in 250 ml. ethyl alcohol containing 0.5 g. 10% palladium-on-charcoal was subjected to a hydrogen atmosphere at 40 p.s.i., while being heated with an infrared lamp and agitated, until uptake of hydrogen ceased. The mixture was filtered, the filtrate was evaporated to dryness under reduced pressure, the resulting residue was dissolved in ether, the ether solution was extracted with dilute potassium bicarbonate, the bicarbonate extract was acidified with 3N-hydrochloric acid and extracted with ether and the ether extract was dried and evaporated to dryness. The resulting residue was crystallized from ether-pentane and a solution of the resulting crystals in 5% potassium bicarbonate solution was acidified with 3N hydrochloric acid and the resulting solid was filtered and washed with water to give 1.3 g. of the title compound; m.p. 70°–80°C.

To an ice cold solution of 28 g. of 9-benzoyl-1,2,3,4-tetrahydrocarbazole-4-carboxylic acid in 100 ml. dry methyl alcohol was added slowly a solution of 4.55 g. of 87% potassium hydroxide in the minimum required amount of dry methyl alcohol. The solution was diluted to one liter with anhydrous ether and the solid which formed on scratching the side of the reaction flask was collected by filtration. A second crop was obtained on further dilution. There was thus obtained 22 g. of potassium 9-benzoyl-1,2,3,4-tetrahydrocarbazole-4-carboxylate; m.p. 254°–256°C. (dec.).

B. Benzyl 9-benzoyl-1,2,3,4-tetrahydrocarbazole-4-carboxylate

To 0.85 g. sodium hydride in 150 ml. of dry dimethylformamide was added, portionwise, 9 g. of benzyl 1,2,3,4-tetrahydrocarbazole-4-carboxylate. The mixture was heated on a steam bath for 15 minutes, the heat was removed, 4 ml. benzoyl chloride was added dropwise to the still hot mixture and heating was resumed for two hours. The mixture, after standing overnight at room temperature, was poured into water containing 4 ml. glacial acetic acid and the resulting mixture was extracted with ether. The ether extract was washed with sodium bicarbonate solution and water, dried, and evaporated to dryness. The resulting residue in 50 ml. dimethylformamide was again treated with 0.42 g. sodium hydride and 2 ml. benzoyl chloride and worked up as described above and the resulting crude product was chromatographed on a 45 mm. by 620 mm. silica gel column using as eluant hexane and hexane containing increasing amounts of ether. There was thus obtained with 7.5% ether in hexane, after evaporation to dryness and recrystallization, 4.6 g. of the title compound; m.p. 107°–109°C. (methyl alcohol).

C. Benzyl 1,2,3,4-tetrahydrocarbazole-4-carboxylate

A stirred mixture of 13 g. 1,2,3,4-tetrahydrocarbazole-4-carboxylic acid, 7.8 g. benzyl chloride and 6.5 g. sodium carbonate in dry dimethylformamide was heated on a steam bath for one hour and filtered. The dimethylformamide was evaporated under reduced pressure and the resulting oil was taken up in ether. The ether solution was washed with water, dried and evaporated to give, after recrystallization, 15.5 g. of the title compound, m.p. 108°–112°C. (heptane).

D. 1,2,3,4-Tetrahydrocarbazole-4-carboxylic acid

To 40 g. 9-benzyl-1,2,3,4-tetrahydrocarbazole-4-carboxylic acid in one liter of liquid ammonia was added, with stirring and portionwise, 8.6 g. of sodium. Ammonium chloride was added portionwise until the blue color of the mixture was dissipated. The ammonia was evaporated, water was added and the mixture was extracted with ether. The aqueous solution was chilled and acidified with dilute hydrochloric acid and the resulting solid was collected by filtration and washed with water to give 23 g. of the title compound; m.p. 163°–165°C. (benzene-methyl alcohol).

E. 9-Benzyl-1,2,3,4-tetrahydrocarbazole-4-carboxylic acid

A mixture of 53 g. of phenylbenzylamine and 30 g. of ethyl 6-bromocyclohexanone-2-carboxylate was maintained in a nitrogen atmosphere at 35° C. for several days. Fused powdered zinc chloride (48 g.) was added and the mixture was heated at 125°–130°C. for 1½ hours. The cooled mixture was slurried in water and extracted with ether. The ether extract was washed with 5% hydrochloric acid and water, dried, and evaporated to dryness to give 38.5 g. crude ethyl ester of the title compound which was treated with a solution of 48 g. potassium hydroxide in 200 ml. water and 200 ml. ethyl alcohol at reflux temperature for three hours. The solution was evaporated to dryness under reduced pressure, the resulting residue was dissolved in water and the aqueous solution was extracted with ether and acidified with 10% hydrochloric acid. The resulting solids were collected and dried to give 27.4 g. of the title compound; m.p. 212°–215°C. (tetrahydrofuran-pentane).

F. Preparation of ethyl 6-bromocyclohexanone-2-carboxylate

To a stirred solution of 31 g. of ethyl cyclohexanone-2-carboxylate in 25 ml. of ether, cooled to −10°C., was added dropwise 35 g. of bromine. Stirring was continued one hour while the solution was allowed to come to room temperature. The solution was poured into ice water containing 20 g. sodium carbonate and was extracted with ether. The ether extract was washed with water, dried and evaporated to dryness to give 23 g. of the title compound; b.p. 88°–91°C. (0.2 mm).

EXAMPLE 35

A. 9-(4-Toluoyl)-1,2,3,4-tetrahydrocarbazole-4-carboxylic acid

Following a procedure similar to that of Example 34A but using the crude benzyl 9-(4-toluoyl)-1,2,3,4-tetrahydrocarbazole-4-carboxylate, from Example 35B below, in 250 ml. ethyl acetate and 0.5 g. of 10% palladium-on-charcoal there was obtained 2.6 g. of the title compound; m.p. 181°–183°C. (ether-hexane).

B. Benzyl 9-(4-toluoyl)-1,2,3,4-tetrahydrocarbazole-4-carboxylate

To a steam bath warmed mixture of 1.5 g sodium hydride in 25 ml. of dry dimethylformamide was added, dropwise and with stirring, 9.15 g. of benzyl 1,2,3,4-tetrahydrocarbazole-4-carboxylate in 25 ml. dry dimethylformamide followed by 5.4 g. of 4-toluoyl chloride in 15 ml. dry dimethylformamide, and heating was continued for two hours. The mixture was cooled and diluted with ether and 1.5 ml. glacial acetic acid. Water was added, the layers were separated and the ether extract was washed with water, 5% potassium bicarbonate solution, 1% aqueous hydrochloric acid and water, and dried over magnesium sulfate. The ether was evaporated to give the title compound which was used without purification in the next step.

EXAMPLE 36

A. 9-Benzoyl-6-methoxy-1,2,3,4-tetrahydrocarbazole-4-carboxylic acid

A solution of 6.7 g. of benzyl 9-benzoyl-6-methoxy-1,2,3,4-tetrahydrocarbazole-4-carboxylate in 250 ml. of ethyl acetate was hydrogenated over 1 g. of palladium-on-charcoal until the required amount of hydrogen had reacted. The mixture was filtered and the filtrate was evaporated to dryness under reduced pressure. The residue was slurried in ether and the resulting solid was collected by filtration to give 1.8 g. of the title compound; m.p. 157–159°C.

B. Benzyl 9-benzoyl-6-methoxy-1,2,3,4-tetrahydrocarbazole-4-carboxylate

Following a procedure similar to that of Example 35B but using 0.67 g. sodium hydride, 37 ml. of dry dimethylformamide, 7.5 g. of benzyl 6-methoxy-1,2,3,4-tetrahydrocarbazole-4-carboxylate, and 2.9 ml. benzoyl chloride there was obtained 10.6 g. of residue which was triturated in hot hexane to give 6.7 g. of the title compound which was used without further purification in the next step.

C. Benzyl 6-methoxy-1,2,3,4-tetrahydrocarbazole-4-carboxylate

Following a procedure similar to that of Example 34C but using 37.2 g. of 6-methoxy-1,2,3,4-tetrahydrocarbazole-4-carboxylic acid, 19.5 g. of benzyl chloride and 16.8 g. of sodium carbonate in 300 ml. of dry dimethylformamide there was obtained 40.3 g. of the title compound; m.p. 81°–83°C. (ethyl alcoholpentane).

D. 6-Methoxy-1,2,3,4-tetrahydrocarbazole-4-carboxylic acid

Following a procedure similar to that of Example 34D but using 32 g. 9-benzyl-6-methoxy-1,2,3,4-tetrahydrocarbazole-4-carboxylic acid, 500 ml. of liquid ammonia and 5 g. of sodium there was obtained 7.7 g. of the title compound; m.p. 175°–177°C. (tetrahydrofuran-hexane). Alternatively the title compound can be prepared by substituting an equivalent amount of 9-(4-chlorobenzyl)-6-methoxy-1,2,3,4-tetrahydrocarbazole-4-carboxylic acid for the 9-benzyl compound in this procedure.

E. 9-Benzyl-6-methoxy-1,2,3,4-tetrahydrocarbazole-4-carboxylic acid

Following a procedure similar to that of Example 34E but using 25 g. of (4-methoxyphenyl)-benzylamine, 12.5 g. ethyl 6-bromocyclohexanone-2-carboxylate and 20 g. of fused powdered zinc chloride; and 20 g. of potassium hydroxide in aqueous methyl alcohol, there was obtained 9.4 g. of the title compound; m.p. 179°–183°C. (isopropyl alcohol-water).

Following a procedure similar to that of Example 36E but substituting for (4-methoxyphenyl)-benzylamine an equivalent amount of (4-methoxyphenyl)-(4-chlorobenzyl)amine there was obtained 9-(4-chlorobenzyl)-6-methoxy-1,2,3,4-tetrahydrocarbazole-4-carboxylic acid; m.p. 218°–220°C. (dimethylformamide-water).

EXAMPLE 37

A. 9-(4-Chlorobenzoyl)-1,2,3,4-tetrahydrocarbazole-4-carboxylic acid

Following a procedure similar to that of Example 36A but using 4.6 g. benzyl 9-(4-chlorobenzoyl)-1,2,3,4-tetrahydrocarbazole-4-carboxylate in 250 ml. of ethyl acetate and 1 g. 10% palladium-on-charcoal there was obtained the title compound which, without further purification, was treated according to the procedure of Example 34A with 0.64 g. of 87% potassium hydroxide in 40 ml. methyl alcohol to give 3 g. of potassium 9-(4-chlorobenzoyl)-1,2,3,4-tetrahydrocarbazole-4-carboxylate; m.p. 244°–247°C.

B. Benzyl 9-(4-chlorobenzoyl)-1,2,3,4-tetrahydrocarbazole-4-carboxylate

Following a procedure similar to that of Example 35B but using 0.8 g. sodium hydride, 90 ml. dimethylformamide, 9.15 g. of benzyl 1,2,3,4-tetrahydrocarbazole-4-carboxylate and 5.4 g. of 4-chlorobenzoylchloride there was obtained 6.2 g. of the title compound; m.p. 123°–124°C. (ethyl alcohol).

EXAMPLE 38

A.
9-(4-Chlorobenzoyl)-6-methoxy-1,2,3,4-tetrahydrocarbazole-4-carboxylic acid

Following a procedure similar to that of Example 36A but using 11 g. of benzyl 9-(4-chlorobenzoyl)-6-methoxy-1,2,3,4-tetrahydrocarbazole-4-carboxylate, from Example 38B below, in 250 ml. ethyl acetate and 1 g. of palladium-on-charcoal there was obtained 5.6 g. of the title compound; m.p. 181°–185°C. (ether).

B. Benzyl 9-(4-chlorobenzoyl)-6-methoxy-1,2,3,4-tetrahydrocarbazole-4-carboxylate Following a procedure similar to that of Example 35B but using 0.85 g. sodium hydride, 50 ml. of dry dimethylformamide, 10 g. of benzyl 6-methoxy-1,2,3,4-tetrahydrocarbazole-4-carboxylate, and 5.8 g. of 4-chlorobenzoyl chloride there was obtained 11 g. of the title compound which was used without purification in the next step.

EXAMPLE 39

A.
9-Benzoyl-6-methyl-1,2,3,4-tetrahydrocarbazole-4-carboxylic acid

Following a procedure similar to that of Example 36A but using 5.9 g. of benzyl 9-benzoyl-6-methyl-1,2,3,4-tetrahydrocarbazole-4-carboxylate in 250 ml. ethyl acetate and 1 g. of palladium-on-charcoal there was obtained 4 g. of the title compound; m.p. 149°–153 °C. (ether-n-hexane).

B. Benzyl 9-benzoyl-6-methyl-1,2,3,4-tetrahydrocarbazole-4-carboxylate

Following a procedure similar to that of Example 35B but using 0.84 g. sodium hydride, 50 ml. of dry dimethylformamide, 9.1 g. of benzyl 6-methyl-1,2,3,4-tetrahydrocarbazole-4-carboxylate, and 4.4 g. of benzoyl chloride, but eliminating the 1% aqueous hydrochloric acid wash subsequent to the bicarbonate wash, there was obtained 8.5 g. of the title compound which was purified by suspension in hot isopropyl alcohol, filtration, followed by suspension in, and filtration from, ether; m.p. 119°–121°C.

C. Benzyl 6-methyl-1,2,3,4-tetrahydrocarbazole-4-carboxylate

Following a procedure similar to that of 34C but using 8.2 g. of 6-methyl-1,2,3,4-tetrahydrocarbazole-4-carboxylic acid, 4.6 g. of benzyl chloride and 4 g. of sodium carbonate in 50 ml. dry dimethylformamide there was obtained 9.1 g. of the title compound; m.p. 115°–117°C. (ethyl alcohol-pentane).

D. 6-Methyl-1,2,3,4-tetrahydrocarbazole-4-carboxylic acid

Following a procedure similar to that of Example 34D but using 27.5 g. of 9-benzyl-6-methyl-1,2,3,4-tetrahydrocarbazole-4-carboxylic acid, 500 ml. of liquid ammonia and 5.9 g. of sodium there was obtained 12.2 g. of the title compound; m.p. 194°–197°C. (acetone-water).

E.
9-Benzyl-6-methyl-1,2,3,4-tetrahydrocarbazole-4-carboxylic acid

Following a procedure similar to that of Example 34E but using 57 g. of (4-tolyl)-benzylamine, 30 g. of ethyl 6-bromocyclohexanone-2-carboxylate and 48 g. of fused powdered zinc chloride; and 20 g. of potassium hydroxide in aqueous ethyl alcohol, there was obtained 33 g. of the title compound; m.p. 200°–208°C. (acetone-water) which on recrystallization from acetone-benzene had m.p. 202°–210°C.

Following a procedure similar to that of Example 31 but substituting in each case for 1-(4-toluoyl)-1-phenylhydrazine hydrochloride an equivalent amount of 1-benzoyl-1-phenylhydrazine hydrochloride and for ethyl cyclohexanone-4-carboxylate an equivalent amount of the following:
methyl cyclohexanone-4-carboxylate;
t-butyl cyclohexanone-4-carboxylate; and
hexyl cyclohexanone-4-carboxylate;
there can be obtained respectively
b-1. methyl 9-benzoyl-1,2,3,4-tetrahydrocarbazole-3-carboxylate;
b-2. t-butyl 9-benzoyl-1,2,3,4-tetrahydrocarbazole-3-carboxylate; and
b-3. hexyl 9-benzoyl-1,2,3,4-tetrahydrocarbazole-3-carboxylate. The intermediate cyclohexanone-4-carboxylates above can be prepared from the corresponding free acids respectively using the standard esterification procedures disclosed hereinabove.

The title compound of Example 1A can alternatively be obtained from the corresponding t-butyl ester (b-2) above by pyrolysis according to the general procedure disclosed hereinabove.

Following a procedure similar to that of Example 1B but substituting in each case for cyclohexanone-4,4-dicarboxylic acid an equivalent amount of cyclohexanone-4-carboxylic acid and for 1-benzoyl-1-phenylhydrazine hydrochloride an equivalent amount of the hydrochlorides of the following:
1-(naphthoyl)-1-phenylhydrazine;
1-(2-naphthoyl)-1-phenylhydrazine;
1-(4-chloro-1-naphthoyl)-1-(4-methoxyphenyl)hydrazine;
1-(6-bromo-2-naphthoyl)-1-(4-chlorophenyl)hydrazine;
1-(4-fluoro-1-naphthoyl)-1-(4-methoxyphenyl)hydrazine;
1-(4-methoxy-1-naphthoyl)-1-phenylhydrazine;
1-(4-dimethylamino-1-naphthoyl)-1-phenylhydrazine; and
1-(4,8-dimethoxy-3-methyl-2-naphthoyl)-1-phenylhydrazine;

there can be obtained respectively
- c-1. 9-(1-naphthoyl)-1,2,3,4-tetrahydrocarbazole-3-carboxylic acid;
- c-2. 9-(2-naphthoyl)-1,2,3,4-tetrahydrocarbazole-3-carboxylic acid;
- c-3. 9-(4-chloro-1-naphthoyl)-6-methoxy-1,2,3,4-tetrahydrocarbazole-3-carboxylic acid;
- c-4. 9-(6-bromo-2-naphthoyl)-6-chloro-1,2,3,4-tetrahydrocarbazole-3-carboxylic acid; c-5. 9-(4-fluoro-1-naphthoyl)-6-methoxy-1,2,3,4-tetrahydrocarbazole-3-carboxylic acid;
- c-6. 9-(4-methoxy-1-naphthoyl)-1,2,3,4-tetrahydrocarbazole-3-carboxylic acid;
- c-7. 9-(4-dimethylamino-1-naphthoyl)-1,2,3,4-tetrahydrocarbazole-3-carboxylic acid; and
- c-8. 9-(4,8-dimethoxy-3-methyl-2-naphthoyl)-1,2,3,4-tetrahydrocarbazole-3-carboxylic acid.

The intermediate 1-naphthoyl-1-phenylhydrazine hydrochlorides above can be prepared from the corresponding naphthoyl chlorides and phenylhydrazines respectively following the general procedure disclosed hereinabove. The naphthoyl chlorides can be obtained from the corresponding known naphthoic acids using the standard procedure disclosed hereinabove.

Alternatively the 9-naphthoyl-1,2,3,4-tetrahydrocarbazole-3-carboxylic acids above (c-1 to c-8) can be obtained by pyrolytic decarboxylation using a procedure similar to that of Example 1A but substituting for 9-benzoyl-1,2,3,4-tetrahydrocarbazole-3,3-dicarboxylic acid an equivalent amount respectively of the following:
- d-1. 9-(1-naphthoyl)-1,2,3,4-tetrahydrocarbazole-3,3-dicarboxylic acid;
- d-2. 9-(2-naphthoyl)-1,2,3,4-tetrahydrocarbazole-3,3-dicarboxylic acid;
- d-3. 9-(4-chloro-1-naphthoyl)-6-methoxy-1,2,3,4-tetrahydrocarbazole-3,3-dicarboxylic acid;
- d-4. 9-(6-bromo-2-naphthoyl)-6-chloro-1,2,3,4-tetrahydrocarbazole-3,3-dicarboxylic acid;
- d-5. 9-(4-fluoro-1-naphthoyl)-6-methoxy-1,2,3,4-tetrahydrocarbazole-3,3-dicarboxylic acid;
- d-6. 9-(4-methoxy-1-naphthoyl)-1,2,3,4-tetrahydrocarbazole-3,3-dicarboxylic acid;
- d-7. 9-(4-dimethylamino-1-naphthoyl)-1,2,3,4-tetrahydrocarbazole-3,3-dicarboxylic acid; and
- d-8. 9-(4,8-dimethoxy-3-methyl-2-naphthoyl)-1,2,3,4-tetrahydrocarbazole-3,3-dicarboxylic acid.

The above intermediate 3,3-dicarboxylic acids (d-1 to d-8) can be prepared by following a procedure similar to that of Example 1B but substituting for 1-benzoyl-1-phenylhydrazine hydrochloride an equivalent amount respectively of the hydrochlorides of the corresponding 1-naphthoyl-1-phenylhydrazines listed above as intermediates in the preparation of compounds c-1 to c-8.

Following a procedure similar to that of Example 1B but substituting in each case for cyclohexanone-4,4-dicarboxylic acid an equivalent amount of cyclohexanone-4-carboxylic acid and for 1-benzoyl-1-phenylhydrazine hydrochloride an equivalent amount of the hydrochlorides of the following:

1-(4-trichloromethoxybenzoyl)-1-(4-hexylphenyl)hydrazine;
1-(4-hexyloxybenzoyl)-1-(4-t-butylphenyl)hydrazine;
1-(4-phenoxybenzoyl)-1-(3-chloro-4-hexylthiophenyl)hydrazine;
1-(4-hexylbenzoyl)-1-(3,5-dibromophenyl)hydrazine;
1-(4-phenylbenzoyl)-1-(4-iodophenyl)hydrazine;
1-[4-(4-phenylbutoxy)benzoyl]-1-[4-(trifluoromethoxy)phenyl]hydrazine;
1-(3,5-dibromo-4-butoxybenzoyl)-1-(3,4-methylenedioxyphenyl)hydrazine;
1-[2-(3-phenylpropyl)benzoyl]-1-phenylhydrazine;
1-[4-(2-phenylpropyl)benzoyl]-1-(4-isopropylthiophenyl)hydrazine;
1-[4-(dimethylamino)benzoyl]-1-(4-isopentyloxyphenyl)hydrazine;
1-(methylthiobenzoyl)-1-(4-benzylphenyl)hydrazine;
1-(4-isopropylthiobenzoyl)-1-(2-chloro-4-hexyloxyphenyl)hydrazine;
1-(2-hexylthiobenzoyl)-1-[3-(5-phenylpentyl)phenyl]hydrazine;
1-[4-(dibutylamino)benzoyl]-1-(3-fluorophenyl)hydrazine;
1-benzoyl-1-[4-(diethylamino)phenyl]hydrazine;
1-benzoyl-1-[4-(dimethylamino)phenyl]hydrazine;
1-[3-(trifluoromethoxy)benzoyl]-1-(4-acetamidophenyl)hydrazine;
1-benzoyl-1-[3-methoxy-4-(6-phenylhexyloxy)phenyl]hydrazine;
1-(3-t-butylsulfinylbenzoyl)-1-phenylhydrazine;
1-(3-t-butylsulfonylbenzoyl)-1-(2-biphenyl)hydrazine;
1-(4-acetamidobenzoyl)-1-(2-phenoxyphenyl)hydrazine;
1-(4-butyramidobenzoyl)-1-(4-methylthiophenyl)hydrazine;
1-benzoyl-1-(4-methylsulfonylphenyl)hydrazine;
1-benzoyl-1-(4-hexylsulfonylphenyl)hydrazine;
1-benzoyl-1-(4-isobutylsulfonylphenyl)hydrazine;
1-benzoyl-1-(3-t-butylsulfinylphenyl)hydrazine;
1-benzoyl-1-(4-methylsulfinylphenyl)hydrazine;
1-benzoyl-1-[4-(trifluoromethyl)phenyl]hydrazine;
1-benzoyl-1-[4-(trichloromethyl)phenyl]hydrazine;
1-(4-benzyloxybenzoyl)-1-phenylhydrazine.
1-(4-nitrobenzoyl)-1-phenylhydrazine;
1-benzoyl-1-(4-nitrophenyl)hydrazine;
1-benzoyl-2',4',6'-trimethyl-2-biphenylhydrazine;
1-benzoyl-4,4'-dichloro-2-biphenylhydrazine;
1-benzoyl-4'-ethoxy-2-biphenylhydrazine;
1-benzoyl-5-fluoro-2-biphenylhydrazine;
1-benzoyl-4'-fluoro-4-biphenylhydrazine;
1-benzoyl-3',5'-dichloro-4'-methoxy-4-biphenylhydrazine;
1-benzoyl-4'-t-butyl-4-biphenylhydrazine; and
1-benzoyl-3'-(trifluoromethyl)-4-biphenylhydrazine;
there can be obtained respectively
- e-1. 9-(4-trichloromethoxybenzoyl)-6-hexyl-1,2,3,4-tetrahydrocarbazole-3-carboxylic acid;
- e-2. 9-(4-hexyloxybenzoyl)6-t-butyl-1,2,3,4-tetrahydrocarbazole-3-carboxylic acid;
- e-3. 9-(4-phenoxybenzoyl)-7-chloro-6-hexylthio-1,2,3,4-tetrahydrocarbazole-3-carboxylic acid;
- e-4. 9-(4-hexylbenzoyl)-5,7-dibromo-1,2,3,4-tetrahydrocarbazole-3-carboxylic acid;
- e-5. 9-(4-phenylbenzoyl)-6-iodo-1,2,3,4-tetrahydrocarbazole-3-carboxylic acid;
- e-6. 9-[4-(4-phenylbutoxy)benzoyl]-6-(trifluoromethoxy)-1,2,3,4-tetrahydrocarbazole-3-carboxylic acid;
- e-7. 9-(3,5-dibromo-4-butoxybenzoyl)-6,7-methylenedioxy-1,2,3,4-tetrahydrocarbazole-3-carboxylic acid;

e-8. 9-[2-(3-phenylpropyl)benzoyl]-1,2,3,4-tetrahydrocarbazole-3-carboxylic acid;

e-9. 9-[4-(2-phenylpropyl)benzoyl]-6-isopropylthio-1,2,3,4-tetrahydrocarbazole-3-carboxylic acid;

e-10. 9-[4-(dimethylamino)benzoyl]-6-isopentyloxy-1,2,3,4-tetrahydrocarbazole-3-carboxylic acid;

e-11. 9-(4-methylthiobenzoyl)-6-benzyl-1,2,3,4-tetrahydrocarbazole-3-carboxylic acid;

e-12. 9-(4-isopropylthiobenzoyl)-8-chloro-6-hexyloxy-1,2,3,4-tetrahydrocarbazole-3-carboxylic acid;

e-13. 9-(2-hexylthiobenzoyl)-5-(5-phenylpentyl)-1,2,3,4-tetrahydrocarbazole-3-carboxylic acid;

e-14. 9-[4-(dibutylamino)benzoyl]-5-fluoro-1,2,3,4-tetrahydrocarbazole-3-carboxylic acid;

e-15. 9-benzoyl-6-(dimethylamino)-1,2,3,4-tetrahydrocarbazole-3-carboxylic acid;

e-16. 9-benzoyl-6-(dimethylamino)-1,2,3,4-tetrahydrocarbazole-3-carboxylic acid;

e-17. 9-[3-(trifluoromethoxy)benzoyl]-6-acetamido-1,2,3,4-tetrahydrocarbazole-3-carboxylic acid;

e-18. 9-benzoyl-7-methoxy-6-(6-phenylhexyloxy)-1,2,3,4-tetrahydrocarbazole-3-carboxylic acid;

e-19. 9-(3-t-butylsulfinylbenzoyl)-1,2,3,4-tetrahydrocarbazole-3-carboxylic acid;

e-20. 9-(3-t-butylsulfonylbenzoyl)-8-phenyl-1,2,3,4-tetrahydrocarbazole-3-carboxylic acid;

e-21. 9-(4-acetamidobenzoyl)-8-phenoxy-1,2,3,4-tetrahydrocarbazole-3-carboxylic acid;

e-22. 9-(4-butyramidobenzoyl)-6-methylthio-1,2,3,4-tetrahydrocarbazole-3-carboxylic acid;

e-23. 9-benzoyl-6-methylsulfonyl-1,2,3,4-tetrahydrocarbazole-3-carboxylic acid;

e-24. 9-benzoyl-6-hexylsulfonyl-1,2,3,4-tetrahydrocarbazole-3-carboxylic acid;

e-25. 9-benzoyl-4-isobutylsulfonyl-1,2,3,4-tetrahydrocarbazole-3-carboxylic acid;

e-26. 9-benzoyl-7-t-butylsulfinyl-1,2,3,4-tetrahydrocarbazole-3-carboxylic acid;

e-27. 9-benzoyl-6-methylsulfinyl-1,2,3,4-tetrahydrocarbazole-3-carboxylic acid;

e-28. 9-benzoyl-6-(trifluoromethyl)-1,2,3,4-tetrahydrocarbazole-3-carboxylic acid;

e-29. 9-benzoyl-6-(trichloromethyl)-1,2,3,4-tetrahydrocarbazole-3-carboxylic acid;

e-30. 9-(4-benzyloxybenzoyl)-1,2,3,4-tetrahydrocarbazole-3-carboxylic acid;

e-31. 9-(4-nitrobenzoyl)-1,2,3,4-tetrahydrocarbazole-3-carboxylic acid;

e-32. 9-benzoyl-6-nitro-1,2,3,4-tetrahydrocarbazole-3-carboxylic acid;

e-33. 9-benzoyl-8-(2,4,6-trimethylphenyl)-1,2,3,4-tetrahydrocarbazole-3-carboxylic acid;

e-34. 9-benzoyl-5-chloro-8-(4-chlorophenyl)-1,2,3,4-tetrahydrocarbazole-3-carboxylic acid;

e-35. 9-benzoyl-8-(4-ethoxyphenyl)-1,2,3,4-tetrahydrocarbazole-3-carboxylic acid;

e-36. 9-benzoyl-6-fluoro-8-phenyl-1,2,3,4-tetrahydrocarbazole-3-carboxylic acid;

e-37. 9-benzoyl-6-(4-fluorophenyl)-1,2,3,4-tetrahydrocarbazole-3-carboxylic acid;

e-38. 9-benzoyl-6-(3,5-dichloro-4-methoxyphenyl)-1,2,3,4-tetrahydrocarbazole-3-carboxylic acid;

e-39. 9-benzoyl-6-(4-t-butylphenyl)-1,2,3,4-tetrahydrocarbazole-3-carboxylic acid; and e-40. 9-benzoyl-6-[3-(trifluoromethyl)phenyl]-1,2,3,4-tetrahydrocarbazole-3-carboxylic acid.

Alternatively the 9-benzoyl-1,2,3,4-tetrahydrocarbazole-3-carboxylic acids above (e-1 to e-32) can be obtained by pyrolytic decarboxylation using a procedure similar to that of Example 1A but substituting for 9-benzoyl-1,2,3,4-tetrahydrocarbazole-3,3-dicarboxylic acid an equivalent amount respectively of the following:

f-1. 9-(4-trichloromethoxybenzoyl)-6-hexyl-1,2,3,4-tetrahydrocarbazole-3,3-dicarboxylic acid;

f-2. 9-(4-hexyloxybenzoyl)-6-t-butyl-1,2,3,4-tetrahydrocarbazole-3,3-dicarboxylic acid;

f-3. 9-(4-phenoxybenzoyl)-7-chloro-6-hexylthio-1,2,3,4-tetrahydrocarbazole-3,3-dicarboxylic acid;

f-4. 9-(4-hexylbenzoyl)-5,7-dibromo-1,2,3,4-tetrahydrocarbazole-3,3-dicarboxylic acid;

f-5. 9-(4-phenylbenzoyl)-6-iodo-1,2,3,4-tetrahydrocarbazole-3,3-dicarboxylic acid;

f-6. 9-[4-(4-phenylbutoxy)benzoyl]-6-(trifluoromethoxy)-1,2,3,4-tetrahydrocarbazole-3,3-dicarboxylic acid;

f-7. 9-(3,5-dibromo-4-butoxybenzoyl)-6,7-methylenedioxy-1,2,3,4-tetrahydrocarbazole-3,3-dicarboxylic acid;

f-8. 9-[2-(3-phenylpropyl)benzoyl]-1,2,3,4-tetrahydrocarbazole-3,3-dicarboxylic acid;

f-9. 9-[4-(2-phenylpropyl)benzoyl]-6-isopropylthio-1,2,3,4-tetrahydrocarbazole-3,3-dicarboxylic acid;

f-10. 9-[4-(dimethylamino)benzoyl]-6-isopentyloxy-1,2,3,4-tetrahydrocarbazole-3,3-dicarboxylic acid;

f-11. 9-(4-methylthiobenzoyl)-6-benzyl-1,2,3,4-tetrahydrocarbazole-3,3-dicarboxylic acid;

f-12. 9-(4-isopropylthiobenzoyl)-8-chloro-6-hexyloxy-1,2,3,4-tetrahydrocarbazole-3,3-dicarboxylic acid;

f-13. 9-(2-hexylthiobenzoyl)-5-(5-phenylpentyl)-1,2,3,4-tetrahydrocarbazole-3,3-dicarboxylic acid;

f-14. 9-[4-(dibutylamino)benzoyl]-5-fluoro-1,2,3,4-tetrahydrocarbazole-3,3-dicarboxylic acid;

f-15. 9-benzoyl-6-(diethylamino)-1,2,3,4-tetrahydrocarbazole-3,3-dicarboxylic acid;

f-16. 9-benzoyl-6-(dimethylamino)-1,2,3,4-tetrahydrocarbazole-3,3-dicarboxylic acid;

f-17. 9[3-(trifluoromethoxy)benzoyl]-6-acetamido-1,2,3,4-tetrahydrocarbazole-3,3-dicarboxylic acid;

f-18. 9-benzoyl-7-methoxy-6-(6-phenylhexyloxy)-1,2,3,4-tetrahydrocarbazole-3,3-dicarboxylic acid;

f-19. 9-(3-t-butylsulfinylbenzoyl)-1,2,3,4-tetrahydrocarbazole-3,3-dicarboxylic acid;

f-20. 9-(3-t-butylsulfonylbenzoyl)-8-phenyl-1,2,3,4-tetrahydrocarbazole-3,3-dicarboxylic acid;

f-21. 9-(4-acetamidobenzoyl)-8-phenoxy-1,2,3,4-tetrahydrocarbazole-3,3-dicarboxylic acid;

f-22. 9-(4-butyramidobenzoyl)-6-methylthio-1,2,3,4-tetrahydrocarbazole-3,3-dicarboxylic acid;

f-23. 9-benzoyl-6-methylsulfonyl-1,2,3,4-tetrahydrocarbazole-3,3-dicarboxylic acid;

f-24. 9-benzoyl-6-hexylsulfonyl-1,2,3,4-tetrahydrocarbazole-3,3-dicarboxylic acid;

f-25. 9-benzoyl-4-isobutylsulfonyl-1,2,3,4-tetrahydrocarbazole-3,3-dicarboxylic acid;

f-26. 9-benzoyl-7-t-butylsulfinyl-1,2,3,4-tetrahydrocarbazole-3,3-dicarboxylic acid;

f-27. 9-benzoyl-6-methylsulfinyl-1,2,3,4-tetrahydrocarbazole-3,3-dicarboxylic acid;

f-28. 9-benzoyl-6-(trifluoromethyl)-1,2,3,4-tetrahydrocarbazole-3,3-dicarboxylic acid;

f-29. 9-benzoyl-6-(trichloromethyl)-1,2,3,4-tetrahydrocarbazole-3,3-dicarboxylic acid;

f-30. 9-(4-benzyloxybenzoyl)-1,2,3,4-tetrahydrocarbazole-3,3-dicarboxylic acid;

f-31. 9-(4-nitrobenzoyl)-1,2,3,4-tetrahydrocarbazole-3,3-dicarboxylic acid; and f-32. 9-benzoyl-6-nitro-1,2,3,4-tetrahydrocarbazole-3,3-dicarboxylic acid.

The above intermediates 3,3-dicarboxylic acids (f-1 to f-32) can be prepared by following a procedure similar to that of Example 1B but substituting for 1-benzoyl-1-phenylhydrazine hydrochloride an equivalent amount respectively of the hydrochlorides of the corresponding 1-benzoyl-1-phenylhydrazines listed above as intermediates for the preparation of compounds e-1 to e-32 inclusive. The intermediate 1-benzoyl-1-phenylhydrazine hydrochlorides listed above can be prepared from the corresponding benzoyl chlorides and corresponding phenylhydrazine using the general procedure disclosed hereinabove. The intermediate benzoyl chlorides and intermediate phenylhydrazines, listed above as intermediates in the preparation of compounds e-1 to e-40 inclusive, are known compounds or can be prepared from the corresponding known benzoic acids and corresponding known anilines respectively using the general procedures disclosed hereinabove.

By using the general procedure described hereinbefore for the hydrogenation of benzyloxy and nitro substituents to hydroxy and amino substituents respectively there can be obtained from 9-benzoyl-6-benzyloxy-1,2,3,4-tetrahydrocarbazole-3-carboxylic acid (Example 30), compounds e-30 to e-32 inclusive above, 9-benzoyl-6-benzyloxy-1,2,3,4-tetrahydrocarbazole-3,3-dicarboxylic acid (a-22) and compounds f-30 to f-32 inclusive above respectively the following:

g-1. 9-benzoyl-6-hydroxy-1,2,3,4-tetrahydrocarbazole-3-carboxylic acid;

g-2. 9-(4-hydroxybenzoyl)-1,2,3,4-tetrahydrocarbazole-3-carboxylic acid;

g-3. 9-(4-aminobenzoyl)-1,2,3,4-tetrahydrocarbazole-3-carboxylic acid;

g-4. 9-benzoyl-6-amino-1,2,3,4-tetrahydrocarbazole-3-carboxylic acid;

g-5. 9-benzoyl-6-hydroxy-1,2,3,4-tetrahydrocarbazole-3,3-dicarboxylic acid;

g-6. 9-(4-hydroxybenzoyl)-1,2,3,4-tetrahydrocarbazole-3,3-dicarboxylic acid;

g-7. 9-(4-aminobenzoyl)-1,2,3,4-tetrahydrocarbazole-3,3-dicarboxylic acid; and g-8. 9-benzoyl-6-amino-1,2,3,4-tetrahydrocarbazole-3,3-dicarboxylic acid.

The 3,3-dicarboxylic acids above (g-5 to g-8) can be converted to the corresponding 3-carboxylic acids (g-1 to g-4 above) by pyrolytic decarboxylation according to a procedure similar to that of Example 1A.

Alternatively, as described hereinabove, the 9-benzoyl-1,2,3,4-tetrahydrocarbazole-3-carboxylic acids can be prepared from their corresponding benzyl esters. Thus, by following a procedure similar to that of Example 34A but substituting for benzyl 9-benzoyl-1,2,3,4-tetrahydrocarbazole-4-carboxylate an equivalent amount of the following:

h-1. benzyl 9-benzoyl-8-phenyl-1,2,3,4-tetrahydrocarbazole-3-carboxylate; and h-2. benzyl 9-benzoyl-6-benzyloxy-1,2,3,4-tetrahydrocarbazole-3-carboxylate there can be obtained respectively i-1. 9-benzoyl-8-phenyl-1,2,3,4-tetrahydrocarbazole-3-carboxylic acid; and i-2. 9-benzoyl-6-hydroxy-1,2,3,4-tetrahydrocarbazole-3-carboxylic acid.

The intermediate benzyl esters h-1 and h-2 above can be prepared by following a procedure similar to that of Example 35B but substituting in each case for 4-toluoyl chloride an equivalent amount of benzoyl chloride and for benzyl 1,2,3,4-tetrahydrocarbazole-4-carboxylate an equivalent amount respectively of the following:

j-1. benzyl 8-phenyl-1,2,3,4-tetrahydrocarbazole-3-carboxylate; and j-2. benzyl 6-benzyloxy-1,2,3,4-tetrahydrocarbazole-3-carboxylate.

The intermediate benzyl esters j-1 and j-2 above can be prepared following a procedure similar to that of Example 34C but substituting for 1,2,3,4-tetrahydrocarbazole-4-carboxylic acid an equivalent amount respectively of the following:

k-1. 8-phenyl-1,2,3,4-tetrahydrocarbazole-3-carboxylic acid; and k-2. 6-benzyloxy-1,2,3,4-tetrahydrocarbazole-3-carboxylic acid.

The above 3-carboxylic acids k-1 [m.p. 219°–222°C. (ethyl acetatehexane)] and k-2 [m.p. 216°–218°C. (acetone-water)] were obtained by following a procedure similar to that of Example 1B but substituting in each case for cyclohexanone-4,4-dicarboxylic acid an equivalent amount of cyclohexanone-4-carboxylic acid and for 1-benzoyl-1-phenylhydrazine hydrochloride an equivalent amount respectively of the hydrochlorides of the following:

2-biphenylylhydrazine; and 4-benzyloxyphenylhydrazine.

8-Phenyl-1,2,3,4-tetrahydrocarbazole-3-carboxylic acid (k-1) was found to be active when tested in rats at 50 mg./kg. of body weight in the Inhibition of Carrageenin-Induced Foot Edema and Adjuvant-Induced Arthritis Test Procedures described hereinbefore and is indicated for use as an antiinflammatory agent.

In a like manner, by following a procedure similar to that of Example 34A, there can be obtained from the benzyl esters l-1 to l-65 inclusive below the corresponding 9-aroyl-1,2,3,4-tetrahydrocarbazole-3-carboxylic acids of Examples 1A to 8A inclusive, Examples 9 to 29 inclusive, c-1 to c-8 inclusive, e-1 to e-18 inclusive, e-28, e-29 and e-33 to 3-40 inclusive respectively:

l-1. 2,4-difluorobenzyl 9-benzoyl-1,2,3,4-tetrahydrocarbazole-3-carboxylate;

l-2. 4-iodobenzyl 9-(4-chlorobenzoyl)-1,2,3,4-tetrahydrocarbazole-3-carboxylate;

l-3. 4-chlorobenzyl 9-benzoyl-6,7-dimethoxy-1,2,3,4-tetrahydrocarbazole-3-carboxylate;

l-4. 4-bromobenzyl 9-(4-toluoyl)-1,2,3,4-tetrahydrocarbazole-3-carboxylate;

l-5. 4-ethylbenzyl 9-(4-fluorobenzoyl)-1,2,3,4-tetrahydrocarbazole-3-carboxylate;

l-6. 4-(1,3-dimethylbutyl)benzyl 9-(4-anisoyl)-1,2,3,4-tetrahydrocarbazole-3-carboxylate;

l-7. 3,4-methylenedioxybenzyl 9-(3,4,5-trimethoxybenzoyl)-1,2,3,4-tetrahydrocarbazole-3-carboxylate;

l-8. 4-isopropoxybenzyl 9-(3-toluoyl)-1,2,3,4-tetrahydrocarbazole-3-carboxylate;

l-9. 3,4,5-trimethoxybenzyl 9-benzoyl-6-methyl-1,2,3,4-tetrahydrocarbazole-3-carboxylate;

l-10. 3,4-dipropoxybenzyl 9-(4-fluorobenzoyl)-6-methyl-1,2,3,4-tetrahydrocarbazole-3-carboxylate;

l-11. 4-methoxy-3,5-dimethylbenzyl 9-[3-(trifluoromethyl)benzoyl]-1,2,3,4-tetrahydrocarbazole-3-carboxylate;
l-12. benzyl 9-(4-t-butylbenzoyl)-1,2,3,4-tetrahydrocarbazole-3-carboxylate;
l-13. benzyl 9-(3-bromobenzoyl)-1,2,3,4-tetrahydrocarbazole-3-carboxylate;
l-14. benzyl 9-benzoyl-6-fluoro-1,2,3,4-tetrahydrocarbazole-3-carboxylate;
l-15. benzyl 9-(4-toluoyl)-6-methyl-1,2,3,4-tetrahydrocarbazole-3-carboxylate;
l-16. benzyl 9-(4-toluoyl)-6-fluoro-1,2,3,4-tetrahydrocarbazole-3-carboxylate;
l-17. benzyl 9-(4-fluorobenzoyl)-6-fluoro-1,2,3,4-tetrahydrocarbazole-3-carboxylate;
l-18. benzyl 9-(4-anisoyl)-6-methyl-1,2,3,4-tetrahydrocarbazole-3-carboxylate;
l-19. benzyl 9-(4-anisoyl)-6-fluoro-1,2,3,4-tetrahydrocarbazole-3-carboxylate;
l-20. benzyl 9-(4-chlorobenzoyl)-6-methoxy-1,2,3,4-tetrahydrocarbazole-3-carboxylate;
l-21. benzyl 9-benzoyl-6-methoxy-1,2,3,4-tetrahydrocarbazole-3-carboxylate;
l-22. benzyl 9-(4-chlorobenzoyl)-6-methyl-1,2,3,4-tetrahydrocarbazole-3-carboxylate;
l-23. benzyl 9-(4-fluorobenzoyl)-6-methoxy-1,2,3,4-tetrahydrocarbazole-3-carboxylate;
l-24. benzyl 9-(4-toluoyl)-6-methoxy-1,2,3,4-tetrahydrocarbazole-3-carboxylate;
l-25. benzyl 9-(3-anisoyl)-1,2,3,4-tetrahydrocarbazole-3-carboxylate;
l-26. benzyl 9-(4-ethoxybenzoyl)-1,2,3,4-tetrahydrocarbazole-3-carboxylate;
l-27. benzyl 9-(3,4-methylenedioxybenzoyl)-1,2,3,4-tetrahydrocarbazole-3-carboxylate;
l-28. benzyl 9-(3-chlorobenzoyl)-1,2,3,4-tetrahydrocarbazole-3-carboxylate;
l-29. benzyl 9-(3-iodobenzoyl)-1,2,3,4-tetrahydrocarbazole-3-carboxylate;
l-30. benzyl 9-(1-naphthoyl)-1,2,3,4-tetrahydrocarbazole-3-carboxylate;
l-31. benzyl 9-(2-naphthoyl)-1,2,3,4-tetrahydrocarbazole-3-carboxylate;
l-32. benzyl 9-(4-chloro-1-naphthoyl)-6-methoxy-1,2,3,4-tetrahydrocarbazole-3-carboxylate;
l-33. benzyl 9-(6-bromo-2-naphthoyl)-6-chloro-1,2,3,4-tetrahydrocarbazole-3-carboxylate;
l-34. benzyl 9-(4-fluoro-1-naphthoyl)-6-methoxy-1,2,3,4-tetrahydrocarbazole-3-carboxylate;
l-35. benzyl 9-(4-methoxy-1-naphthoyl)-1,2,3,4-tetrahydrocarbazole-3-carboxylate;
l-36. benzyl 9-(4-dimethylamino-1-naphthoyl)-1,2,3,4-tetrahydrocarbazole-3-carboxylate;
l-37. benzyl 9-(4,8-dimethoxy-3-methyl-2-naphthoyl)-1,2,3,4-tetrahydrocarbazole-3-carboxylate;
l-38. benzyl 9-(4-trichloromethoxybenzoyl)-6-hexyl-1,2,3,4-tetrahydrocarbazole-3-carboxylate;
l-39. benzyl 9-(4-hexyloxybenzoyl)-6-t-butyl-1,2,3,4-tetrahydrocarbazole-3-carboxylate;
l-40. benzyl 9-(4-phenoxybenzoyl)-7-chloro-6-hexylthio-1,2,3,4-tetrahydrocarbazole-3-carboxylate;
l-41. benzyl 9-(4-hexylbenzoyl)-5,7-dibromo-1,2,3,4-tetrahydrocarbazole-3-carboxylate;
l-42. benzyl 9-(4-phenylbenzoyl)-6-iodo-1,2,3,4-tetrahydrocarbazole-3-carboxylate;
l-43. benzyl 9-[4-(4-phenylbutoxy)benzoyl]-6-(trifluoromethoxy)-1,2,3,4-tetrahydrocarbazole-3-carboxylate;
l-44. benzyl 9-(3,5-dibromo-4-butoxybenzoyl)-6,7-methylenedioxy-1,2,3,4-tetrahydrocarbazole-3-carboxylate;
l-45. benzyl 9-[2-(3-phenylpropyl)benzoyl]-1,2,3,4-tetrahydrocarbazole-3-carboxylate;
l-46. benzyl 9-[4-(2-phenylpropyl)benzoyl]-6-isopropylthio-1,2,3,4-tetrahydrocarbazole-3-carboxylate;
l-47. benzyl 9-[4-(dimethylamino)benzoyl]-6-isopentyloxy-1,2,3,4-tetrahydrocarbazole-3-carboxylate;
l-48. benzyl 9-(4-methylthiobenzoyl)-6-benzyl-1,2,3,4-tetrahydrocarbazole-3-carboxylate;
l-49. benzyl 9-(4-isopropylthiobenzoyl)-8-chloro-6-hexyloxy-1,2,3,4-tetrahydrocarbazole-3-carboxylate;
l-50. benzyl 9-(2-hexylthiobenzoyl)-5-(5-phenylpentyl)-1,2,3,4-tetrahydrocarbazole-3-carboxylate;
l-51. benzyl 9-[4-(dibutylamino)benzoyl]-5-fluoro-1,2,3,4-tetrahydrocarbazole-3-carboxylate;
l-52. benzyl 9-benzoyl-6-(diethylamino)-1,2,3,4-tetrahydrocarbazole-3-carboxylate;
l-53. benzyl 9-benzoyl-6-(dimethylamino)-1,2,3,4-tetrahydrocarbazole-3-carboxylate;
l-54. benzyl 9-[3-(trifluoromethoxy)benzoyl]-6-acetamido-1,2,3,4-tetrahydrocarbazole-3-carboxylate;
l-55. benzyl 9-benzoyl-7-methoxy-6-(6-phenylhexyloxy)-1,2,3,4-tetrahydrocarbazole-3-carboxylate;
l-56. benzyl 9-benzoyl-6-(trifluoromethyl)-1,2,3,4-tetrahydrocarbazole-3-carboxylate;
l-57. benzyl 9-benzoyl-6-(trichloromethyl)-1,2,3,4-tetrahydrocarbazole-3-carboxylate;
l-58. benzyl 9-benzoyl-8-(2,4,6-trimethylphenyl)-1,2,3,4-tetrahydrocarbazole-3-carboxylate;
l-59. benzyl 9-benzoyl-5-chloro-8-(4-chlorophenyl)-1,2,3,4-tetrahydrocarbazole-3-carboxylate;
l-60. benzyl 9-benzoyl-8-(4-ethoxyphenyl)-1,2,3,4-tetrahydrocarbazole-3-carboxylate;
l-61. benzyl 9-benzoyl-6-fluoro-8-phenyl-1,2,3,4-tetrahydrocarbazole-3-carboxylate;
l-62. benzyl 9-benzoyl-6-(4-fluorophenyl)-1,2,3,4-tetrahydrocarbazole-3-carboxylate;
l-63. benzyl 9-benzoyl-6-(3,5-dichloro-4-methoxyphenyl)-1,2,3,4-tetrahydrocarbazole-3-carboxylate;
l-64. benzyl 9-benzoyl-6-(4-t-butylphenyl)-1,2,3,4-tetrahydrocarbazole-3-carboxylate; and
l-65. benzyl 9-benzoyl-6-[3-(trifluoromethyl)phenyl]-1,2,3,4-tetrahydrocarbazole-3-carboxylate.

The intermediate benzyl 9-aroyl-1,2,3,4-tetrahydrocarbazole-3-carboxylates (l-1 to l-65) above can be obtained by following a procedure similar to that of Example 35B but using equivalent amounts of the appropriate benzoyl chloride or naphthoyl chloride and the appropriate benzyl 1,2,3,4-tetrahydrocarbazole-3-carboxylate; the intermediate benzyl 1,2,3,4-tetrahydrocarbazole-3-carboxylates, with the numbers of the corresponding products which can be obtained therefrom given in parenthesis, are as follows:

m-1. 2,4-difluorobenzyl 1,2,3,4-tetrahydrocarbazole-3-carboxylate (l-1);
m-2. 4-iodobenzyl 1,2,3,4-tetrahydrocarbazole-3-carboxylate (l-2);
m-3. 4-chlorobenzyl 6,7-dimethoxy-1,2,3,4-tetrahydrocarbazole-3-carboxylate (l-3);

m-4. 4-bromobenzyl 1,2,3,4-tetrahydrocarbazole-3-carboxylate (I-4);
m-5. 4-ethylbenzyl 1,2,3,4-tetrahydrocarbazole-3-carboxylate (I-5);
m-6. 4-(1,3-dimethylbutyl)benzyl 1,2,3,4-tetrahydrocarbazole-3-carboxylates (I-6);
m-7. 3,4-methylenedioxybenzyl 1,2,3,4-tetrahydrocarbazole-3-carboxylate (I-7);
m-8. 4-isopropoxybenzyl 1,2,3,4-tetrahydrocarbazole-3-carboxylate (I-8);
m-9. 3,4,5-trimethoxybenzyl 6-methyl-1,2,3,4-tetrahydrocarbazole-3-carboxylate (I-9);
m-10. 3,4-dipropoxybenzyl 6-methyl-1,2,3,4-tetrahydrocarbazole-3-carboxylate (I-10);
m-11. 4-methoxy-3,5-dimethylbenzyl 1,2,3,4-tetrahydrocarbazole-3-carboxylate (I-11);
m-12. benzyl 1,2,3,4-tetrahydrocarbazole-3-carboxylate (I-12, I-13, I-25 to I-31 inclusive, I-35, I-36, I-37 and I-45);
m-13. benzyl 6-fluoro-1,2,3,4-tetrahydrocarbazole-3-carboxylate (I-14, I-16, I-17 and I-19);
m-14. benzyl 6-methyl-1,2,3,4-tetrahydrocarbazole-3-carboxylate (I-15, I-18 and I-22);
m-15. benzyl 6-methoxy-1,2,3,4-tetrahydrocarbazole-3-carboxylate (I-20, I-21, I-23, I-24, I-32 and I-34);
m-16. benzyl 6-chloro-1,2,3,4-tetrahydrocarbazole-3-carboxylate (I-33);
m-17. benzyl 6-hexyl-1,2,3,4-tetrahydrocarbazole-3-carboxylate (I-38);
m-18. benzyl 6-t-butyl-1,2,3,4-tetrahydrocarbazole-3-carboxylate (I-39);
m-19. benzyl 7-chloro-6-hexylthio-1,2,3,4-tetrahydrocarbazole-3-carboxylate (I-40);
m-20. benzyl 5,7-dibromo-1,2,3,4-tetrahydrocarbazole-3-carboxylate (I-41);
m-21. benzyl 6-iodo-1,2,3,4-tetrahydrocarbazole-3-carboxylate (I-42);
m-22. benzyl 6-(trifluoromethoxy)-1,2,3,4-tetrahydrocarbazole-3-carboxylate (I-43);
m-23. benzyl 6,7-methylenedioxy-1,2,3,4-tetrahydrocarbazole-3-carboxylate (I-44);
m-24. benzyl 6-isopropylthio-1,2,3,4-tetrahydrocarbazole-3-carboxylate (I-46);
m-25. benzyl 6-isopentyloxy-1,2,3,4-tetrahydrocarbazole-3-carboxylate (I-47);
m-26. benzyl 6-benzyl-1,2,3,4-tetrahydrocarbazole-3-carboxylate (I-48);
m-27. benzyl 8-chloro-6-hexyloxy-1,2,3,4-tetrahydrocarbazole-3-carboxylate (I-49);
m-28. benzyl 5-(5-phenylpentyl)-1,2,3,4-tetrahydrocarbazole-3-carboxylate (I-50);
m-29. benzyl 5-fluoro-1,2,3,4-tetrahydrocarbazole-3-carboxylate (I-51);
m-30. benzyl 6-(diethylamino)-1,2,3,4-tetrahydrocarbazole-3-carboxylate (I-52);
m-31. benzyl 6-dimethylamino)-1,2,3,4-tetrahydrocarbazole-3-carboxylate (I-53);
m-32. benzyl 6-acetamido-1,2,3,4-tetrahydrocarbazole-3-carboxylate (I-54);
m-33. benzyl 7-methoxy-6-(6-phenylhexyloxy)-1,2,3,4-tetrahydrocarbazole-3-carboxylate (I-55);
m-34. benzyl 6-(trifluoromethyl)-1,2,3,4-tetrahydrocarbazole-3-carboxylate (I-56);
m-35. benzyl 6-(trichloromethyl)-1,2,3,4-tetrahydrocarbazole-3-carboxylate (I-57);
m-36. benzyl 8-(2,4,6-trimethylphenyl)-1,2,3,4-tetrahydrocarbazole-3-carboxylate (I-58);
m-37. benzyl 5-chloro-8-(4-chlorophenyl)-1,2,3,4-tetrahydrocarbazole-3-carboxylate (I-59);
m-38. benzyl 8-(4-ethoxyphenyl)-1,2,3,4-tetrahydrocarbazole-3-carboxylate (I-60);
m-39. benzyl 6-fluoro-8-phenyl-1,2,3,4-tetrahydrocarbazole-3-carboxylate (I-61);
m-40. benzyl 6-(4-fluorophenyl)-1,2,3,4-tetrahydrocarbazole-3-carboxylate (I-62);
m-41. benzyl 6-(3,5-dichloro-4-methoxyphenyl)-1,2,3,4-tetrahydrocarbazole-3-carboxylate (I-63);
m-42. benzyl 6-(4-t-butylphenyl)-1,2,3,4-tetrahydrocarbazole-3-carboxylate (I-64); and
m-43. benzyl 6-[3-(trifluoromethyl)phenyl]-1,2,3,4-tetrahydrocarbazole-3-carboxylate (I-65).

The intermediate benzyl 9-H-1,2,3,4-tetrahydrocarbazole-3-carboxylates (m-1 to m-43 above) can be obtained by following a procedure similar to that of Example 34C but using equivalent amounts of the appropriate 1,2,3,4-tetrahydrocarbazole-3-carboxylic acid (n-1 to n-33 below) and appropriate benzyl chloride.

n-1. 1,2,3,4-tetrahydrocarbazole-3-carboxylic acid;
n-2. 6,7-dimethoxy-1,2,3,4-tetrahydrocarbazole-3-carboxylic acid;
n-3. 6-methyl-1,2,3,4-tetrahydrocarbazole-3-carboxylic acid;
n-4. 6-fluoro-1,2,3,4-tetrahydrocarbazole-3-carboxylic acid;
n-5. 6-methoxy-1,2,3,4-tetrahydrocarbazole-3-carboxylic acid [m.p. 202°–205°C. (acetone)];
n-6. 6-chloro-1,2,3,4-tetrahydrocarbazole-3-carboxylic acid;
n-7. 6-hexyl-1,2,3,4-tetrahydrocarbazole-3-carboxylic acid;
n-8. 6-t-butyl-1,2,3,4-tetrahydrocarbazole-3-carboxylic acid;
n-9. 7-chloro-6-hexylthio-1,2,3,4-tetrahydrocarbazole-3-carboxylic acid;
n-10. 5,7-dibromo-1,2,3,4-tetrahydrocarbazole-3-carboxylic acid;
n-11. 6-iodo-1,2,3,4-tetrahydrocarbazole-3-carboxylic acid;
n-12. 6-(trifluoromethoxy)-1,2,3,4-tetrahydrocarbazole-3-carboxylic acid;
n-13. 6,7-methylenedioxy-1,2,3,4-tetrahydrocarbazole-3-carboxylic acid;
n-14. 6-isopropylthio-1,2,3,4-tetrahydrocarbazole-3-carboxylic acid;
n-15. 6-isopentyloxy-1,2,3,4-tetrahydrocarbazole-3-carboxylic acid;
n-16. 6-benzyl-1,2,3,4-tetrahydrocarbazole-3-carboxylic acid;
n-17. 8-chloro-6-hexyloxy-1,2,3,4-tetrahydrocarbazole-3-carboxylic acid;
n-18. 5-(5-phenylpentyl)-1,2,3,4-tetrahydrocarbazole-3-carboxylic acid;
n-19. 5-fluoro-1,2,3,4-tetrahydrocarbazole-3-carboxylic acid;
n-20. 6-(diethylamino)-1,2,3,4-tetrahydrocarbazole-3-carboxylic acid;
n-21. 6-(dimethylamino)-1,2,3,4-tetrahydrocarbazole-3-carboxylic acid;
n-22. 6-acetamido-1,2,3,4-tetrahydrocarbazole-3-carboxylic acid;
n-23. 7-methoxy-6-(6-phenylhexyloxy)-1,2,3,4-tetrahydrocarbazole-3-carboxylic acid;
n-24. 6-(trifluoromethyl)-1,2,3,4-tetrahydrocarbazole-3-carboxylic acid;

n-25. 6-(trichloromethyl)-1,2,3,4-tetrahydrocarbazole-3-carboxylic acid;
n-26. 8-(2,4,6-trimethylphenyl)-1,2,3,4-tetrahydrocarbazole-3-carboxylic acid;
n-27. 5-chloro-8-(4-chlorophenyl)-1,2,3,4-tetrahydrocarbazole-3-carboxylic acid;
n-28. 8-(4-ethoxyphenyl)-1,2,3,4-tetrahydrocarbazole-3-carboxylic acid;
n-29. 6-fluoro-8-phenyl-1,2,3,4-tetrahydrocarbazole-3-carboxylic acid;
n-30. 6-(4-fluorophenyl)-1,2,3,4-tetrahydrocarbazole-3-carboxylic acid;
n-31. 6-(3,5-dichloro-4-methoxyphenyl)-1,2,3,4-tetrahydrocarbazole-3-carboxylic acid;
n-32. 6-(4-t-butylphenyl)-1,2,3,4-tetrahydrocarbazole-3-carboxylic acid; and
n-33. 6-[3-(trifluoromethyl)phenyl]-1,2,3,4-tetrahydrocarbazole-3-carboxylic acid.

The intermediate 1,2,3,4-tetrahydrocarbazole-3-carboxylic acids (n-1 to n-33 above) can be obtained by following a procedure similar to that of Example 1B but using equivalent amounts of the appropriate phenylhydrazine hydrochloride and, in each case, cyclohexanone-4-carboxylic acid.

Following a procedure similar to that described in Example 1B but substituting for cyclohexanone-4,4-dicarboxylic acid an equivalent amount of 4-methylcyclohexanone-4-carboxylic acid there can be obtained 9-benzoyl-3-methyl-1,2,3,4-tetrahydrocarbazole-3-carboxylic acid.

Following a procedure similar to that of Example 34A but substituting for benzyl 9-benzoyl-1,2,3,4-tetrahydrocarbazole-4-carboxylate an equivalent amount of the following:

o-1. benzyl 9-(1-naphthoyl)-1,2,3,4-tetrahydrocarbazole-4-carboxylate;
o-2. benzyl 9-(2-naphthoyl)-1,2,3,4-tetrahydrocarbazole-4-carboxylate;
o-3. benzyl 9-(4-chloro-1-naphthoyl)-1,2,3,4-tetrahydrocarbazole-4-carboxylate;
o-4. benzyl 9-(6-bromo-2-naphthoyl)-1,2,3,4-tetrahydrocarbazole-4-carboxylate;
o-5. benzyl 9-(4-fluoro-1-naphthoyl)-1,2,3,4-tetrahydrocarbazole-4-carboxylate;
o-6. benzyl 9-(4-methoxy-1-naphthoyl)-1,2,3,4-tetrahydrocarbazole-4-carboxylate;
o-7. benzyl 9-(4-dimethylamino-1-naphthoyl)-1,2,3,4-tetrahydrocarbazole-4-carboxylate; and
o-8. benzyl 9-(4,8-dimethoxy-3-methyl-2-naphthoyl)-1,2,3,4-tetrahydrocarbazole-4-carboxylate;

there can be obtained respectively
p-1. 9-(1-naphthoyl)-1,2,3,4-tetrahydrocarbazole-4-carboxylic acid;
p-2. 9-(2-naphthoyl)-1,2,3,4-tetrahydrocarbazole-4-carboxylic acid;
p-3. 9-(4-chloro-1-naphthoyl)-1,2,3,4-tetrahydrocarbazole-4-carboxylic acid;
p-4. 9-(6-bromo-2-naphthoyl)-1,2,3,4-tetrahydrocarbazole-4-carboxylic acid;
p-5. 9-(4-fluoro-1-naphthoyl)-1,2,3,4-tetrahydrocarbazole-4-carboxylic acid;
p-6. 9-(4-methoxy-1-naphthoyl)-1,2,3,4-tetrahydrocarbazole-4-carboxylic acid;
p-7. 9-(4-dimethylamino-1-naphthoyl)-1,2,3,4-tetrahydrocarbazole-4-carboxylic acid; and
p-8. 9-(4,8-dimethoxy-3-methyl-2-naphthoyl)-1,2,3,4-tetrahydrocarbazole-4-carboxylic acid.

The intermediate benzyl 9-naphthoyl-1,2,3,4-tetrahydrocarbazole-4-carboxylates (o-1 to o-8 above) can be prepared by following a procedure similar to that of Example 35B but substituting respectively for 4-toluoyl chloride an equivalent amount of the following:
1-naphthoyl chloride;
2-naphthoyl chloride;
4-chloro-1-naphthoyl chloride;
6-bromo-2-naphthoyl chloride;
4-fluoro-1-naphthoyl chloride;
4-methoxy-1-naphthoyl chloride;
4-dimethylamino-1-naphthoyl chloride; and
4,8-dimethoxy-3-methyl-2-naphthoyl chloride.

The naphthoyl chlorides listed above can be prepared from the corresponding known naphthoic acids according to the general procedures disclosed hereinabove.

Following a procedure similar to that of Example 35B but substituting in each case for 4-toluoyl chloride an equivalent amount of benzoyl chloride and for benzyl-1,2,3,4-tetrahydrocarbazole-4-carboxylate an equivalent amount of the following:
methyl 1,2,3,4-tetrahydrocarbazole-4-carboxylate;
t-butyl 1,2,3,4-tetrahydrocarbazole-4-carboxylate; and
hexyl 1,2,3,4-tetrahydrocarbazole-4-carboxylate;
there can be obtained respectively
q-1. methyl 9-benzoyl-1,2,3,4-tetrahydrocarbazole-4-carboxylate;
q-2. t-butyl 9-benzoyl-1,2,3,4-tetrahydrocarbazole-4-carboxylate; and
q-3. hexyl 9-benzoyl-1,2,3,4-tetrahydrocarbazole-4-carboxylate.

The intermediate methyl, t-butyl and hexyl esters of 1,2,3,4-tetrahydrocarbazole-4-carboxylic acid can be prepared from the corresponding free acid using the known esterification procedures disclosed hereinabove.

The title compound of Example 34A can alternatively be obtained from t-butyl 9-benzoyl-1,2,3,4-tetrahydrocarbazole-4-carboxylate (q-2) by pyrolysis according to the general procedure disclosed hereinabove.

Following a procedure similar to that of Example 34A but substituting for benzyl 9-benzoyl-1,2,3,4-tetrahydrocarbazole-4-carboxylate an equivalent amount of the following:

r-1. 2,4-difluorobenzyl 9-(4-chlorobenzoyl)-6-fluoro-1,2,3,4-tetrahydrocarbazole-4-carboxylate;
r-2. 4-iodobenzyl 9-(4-trichloromethoxybenzoyl)-6-hexyl-1,2,3,4-tetrahydrocarbazole-4-carboxylate;
r-3. 4-chlorobenzyl 9-(4-hexyloxybenzoyl)-6-t-butyl-1,2,3,4-tetrahydrocarbazole-4-carboxylate;
r-4. 4-bromobenzyl 9-(4-phenoxybenzoyl)-7-chloro-6-hexylthio-1,2,3,4-tetrahydrocarbazole-4-carboxylate;
r-5. 4-ethylbenzyl 9-(4-hexylbenzoyl)-5,7-dibromo-1,2,3,4-tetrahydrocarbazole-4-carboxylate;
r-6. 4-(1,3-dimethylbutyl)benzyl 9-(4-phenylbenzoyl)-6-iodo-1,2,3,4-tetrahydrocarbazole-4-carboxylate;
r-7. 3,4-methylenedioxybenzyl 9-[4-(4-phenylbutoxy)-benzoyl]-6-(trifluoromethoxy)-1,2,3,4-tetrahydrocarbazole-4-carboxylate;
r-8. 4-isopropoxybenzyl 9-(3,5-dibromo-4-butoxybenzoyl)-6,7-methylenedioxy-1,2,3,4-tetrahydrocarbazole-4-carboxylate;

r-9. 3,4,5-trimethoxybenzyl 9-[2-(3-phenylbutoxy)-benzoyl]-6-methyl-1,2,3,4-tetrahydrocarbazole-4-carboxylate;

r-10. 3,4-dipropoxybenzyl[4-(2-phenylpropyl)benzoyl]-6-isopropylthio-1,2,3,4-tetrahydrocarbazole-4-carboxylate;

r-11. 4-methoxy-3,5-dimethylbenzyl 9-[4-(dimethylamino)benzoyl]-6-isopentyloxy-1,2,3,4-tetrahydrocarbazole-4-carboxylate;

r-12. benzyl 9-(4-methylthiobenzoyl)-6-benzyl-1,2,3,4-tetrahydrocarbazole-4-carboxylate;

r-13. benzyl 9-(4-isopropylthiobenzoyl)-8-chloro-6-hexyloxy-1,2,3,4-tetrahydrocarbazole-4-carboxylate;

r-14. benzyl 9-(2-hexylthiobenzoyl)-5-(5-phenylpentyl)-1,2,3,4-tetrahydrocarbazole-4-carboxylate;

r-15. benzyl 9-[4-(dibutylamino)benzoyl]-5-fluoro-1,2,3,4-tetrahydrocarbazole-4-carboxylate;

r-16. benzyl 9-(4-t-butylbenzoyl)-6-(diethylamino)-1,2,3,4-tetrahydrocarbazole-4-carboxylate;

r-17. benzyl 9-(4-methoxybenzoyl)-6-(dimethylamino)-1,2,3,4-tetrahydrocarbazole-4-carboxylate;

r-18. benzyl 9-[3-(trifluoromethoxy)benzoyl]-1,2,3,4-tetrahydrocarbazole-4-carboxylate;

r-19. benzyl 9-benzoyl-7-methoxy-6-(6-phenylhexyloxy)-1,2,3,4-tetrahydrocarbazole-4-carboxylate;

r-20. benzyl 9-(4-fluorobenzoyl)-8-phenyl-1,2,3,4-tetrahydrocarbazole-4-carboxylate;

r-21. benzyl 9-(3,4-methylenedioxybenzoyl)-8-phenoxy-1,2,3,4-tetrahydrocarbazole-4-carboxylate;

r-22. benzyl 9-(3-iodobenzoyl)-6-methylthio-1,2,3,4-tetrahydrocarbazole-4-carboxylate;

r-23. benzyl 9-benzoyl-6-(trifluoromethyl)-1,2,3,4-tetrahydrocarbazole-4-carboxylate;

r-24. benzyl 9-benzoyl-6-(trichloromethyl)-1,2,3,4-tetrahydrocarbazole-4-carboxylate;

r-25. benzyl 9-(4-chlorobenzoyl)-6-methyl-1,2,3,4-tetrahydrocarbazole-4-carboxylate; and r-26. benzyl 9-(4-benzyloxybenzoyl)-1,2,3,4-tetrahydrocarbazole-4-carboxylate;

there can be obtained respectively s-1. 9-(4-chlorobenzoyl)-6-fluoro-1,2,3,4-tetrahydrocarbazole-4-carboxylic acid;

s-2. 9-(4-trichloromethoxybenzoyl)-6-hexyl-1,2,3,4-tetrahydrocarbazole-4-carboxylic acid;

s-3. 9-(4-hexyloxybenzoyl)-6-t-butyl-1,2,3,4-tetrahydrocarbazole-4-carboxylic acid;

s-4. 9-(4-phenoxybenzoyl)-7-chloro-6-hexylthio-1,2,3,4-tetrahydrocarbazole-4-carboxylic acid;

s-5. 9-(4-hexylbenzoyl)-5,7-dibromo-1,2,3,4-tetrahydrocarbazole-4-carboxylic acid;

s-6. 9-(4-phenylbenzoyl)-6-iodo-1,2,3,4-tetrahydrocarbazole-4-carboxylic acid;

s-7. 9-[4-(4-phenylbutoxy)benzoyl]-6-(trifluoromethoxy)-1,2,3,4-tetrahydrocarbazole-4-carboxylic acid;

s-8. 9-(3,5-dibromo-4-butoxybenzoyl)-6,7-methylenedioxy-1,2,3,4-tetrahydrocarbazole-4-carboxylic acid;

s-9. 9-[2-(3-phenylpropyl)benzoyl]-6-methyl-1,2,3,4-tetrahydrocarbazole-4-carboxylic acid;

s-10. 9-[4-(2-phenylpropyl)benzoyl]-6-isopropylthio-1,2,3,4-tetrahydrocarbazole-4-carboxylic acid;

s-11. 9-[4-(dimethylamino)benzoyl]-6-isopentyloxy-1,2,3,4-tetrahydrocarbazole-4-carboxylic acid;

s-12. 9-(4-methylthiobenzoyl)-6-benzyl-1,2,3,4-tetrahydrocarbazole-4-carboxylic acid;

s-13. 9-(4-isopropylthiobenzoyl)-8-chloro-6-hexyloxy-1,2,3,4-tetrahydrocarbazole-4-carboxylic acid;

s-14. 9-(2-hexylthiobenzoyl)-5-(5-phenylpentyl)-1,2,3,4-tetrahydrocarbazole-4-carboxylic acid;

s-15. 9-[4-(dibutylamino)benzoyl]-5-fluoro-1,2,3,4-tetrahydrocarbazole-4-carboxylic acid;

s-16. 9-(4-t-butylbenzoyl)-6-(diethylamino)-1,2,3,4-tetrahydrocarbazole-4-carboxylic acid;

s-17. 9-(4-methoxybenzoyl)-6-(dimethylamino)-1,2,3,4-tetrahydrocarbazole-4-carboxylic acid;

s-18. 9-[3-(trifluoromethoxy)benzoyl]-1,2,3,4-tetrahydrocarbazole-4-carboxylic acid;

s-19. 9-benzoyl-7-methoxy-6-(6-phenylhexyloxy)-1,2,3,4-tetrahydrocarbazole-4-carboxylic acid;

s-20. 9-(4-fluorobenzoyl)-8-phenyl-1,2,3,4-tetrahydrocarbazole-4-carboxylic acid;

s-21. 9-(3,4-methylenedioxybenzoyl)-8-phenoxy-1,2,3,4-tetrahydrocarbazole-4-carboxylic acid;

s-22. 9-(3-iodobenzoyl)-6-methylthio-1,2,3,4-tetrahydrocarbazole-4-carboxylic acid;

s-23. 9-benzoyl-6-(trifluoromethyl)-1,2,3,4-tetrahydrocarbazole-4-carboxylic acid;

s-24. 9-benzoyl-6-(trichloromethyl)-1,2,3,4-tetrahydrocarbazole-4-carboxylic acid;

s-25. 9-(4-chlorobenzoyl)-6-methyl-1,2,3,4-tetrahydrocarbazole-4-carboxylic acid; and s-26. 9-(4-hydroxybenzoyl)-1,2,3,4-tetrahydrocarbazole-4-carboxylic acid.

The intermediate benzyl 9-benzoyl-1,2,3,4-tetrahydrocarbazole-4-carboxylates (r-1 to r-26 above) can be obtained by following a procedure similar to that of Example 35B but using equivalent amounts of the appropriate benzoyl chloride and the appropriate benzyl-1,2,3,4-tetrahydrocarbazole-4-carboxylate; the intermediate benzyl 1,2,3,4-tetrahydrocarbazole-4-carboxylates, with the numbers of the corresponding products which can be obtained therefrom given in parenthesis, are as follows:

t-1. 2,4-difluorobenzyl 6-fluoro-1,2,3,4-tetrahydrocarbazole-4-carboxylate (r-1);

t-2. 4-iodobenzyl 6-hexyl-1,2,3,4-tetrahydrocarbazole-4-carboxylate (r-2);

t-3. 4-chlorobenzyl 6-t-butyl-1,2,3,4-tetrahydrocarbazole-4-carboxylate (r-3);

t-4. 4-bromobenzyl 7-chloro-6-hexylthio-1,2,3,4-tetrahydrocarbazole-4-carboxylate (r-4);

t-5. 4-ethylbenzyl 5,7-dibromo-1,2,3,4-tetrahydrocarbazole-4-carboxylate (r-5);

t-6. 4-(1,3-dimethylbutyl)benzyl 6-iodo-1,2,3,4-tetrahydrocarbazole-4-carboxylate (r-6);

t-7. 3,4-methylenedioxybenzyl 6-(trifluoromethoxy)-1,2,3,4-tetrahydrocarbazole-4-carboxylate (r-7);

t-8. 4-isopropoxybenzyl 6,7-methylenedioxy-1,2,3,4-tetrahydrocarbazole-4-carboxylate (r-8);

t-9. 3,4,5-trimethoxybenzyl 6-methyl-1,2,3,4-tetrahydrocarbazole-4-carboxylate (r-9);

t-10. 3,4-dipropoxybenzyl 6-isopropylthio-1,2,3,4-tetrahydrocarbazole-4-carboxylate (r-10);

t-11. 4-methoxy-3,5-dimethylbenzyl 6-isopentyloxy-1,2,3,4-tetrahydrocarbazole-4-carboxylate (r-11);

t-12. benzyl 6-benzyl-1,2,3,4-tetrahydrocarbazole-4-carboxylate (r-12);

t-13. benzyl 8-chloro-6-hexyloxy-1,2,3,4-tetrahydrocarbazole-4-carboxylate (r-13);

t-14. benzyl 5-(5-phenylphenyl)-1,2,3,4-tetrahydrocarbazole-4-carboxylate (r-14);
t-15. benzyl 5-fluoro-1,2,3,4-tetrahydrocarbazole-4-carboxylate (r-15);
t-16. benzyl 6-(diethylamino)-1,2,3,4-tetrahydrocarbazole-4-carboxylate (r-16);
t-17. benzyl 6-(dimethylamino)-1,2,3,4-tetrahydrocarbazole-4-carboxylate (r-17);
t-18. benzyl 1,2,3,4-tetrahydrocarbazole-4-carboxylate (r-18 and r-26);
t-19. benzyl 7-methoxy-6-(6-phenylhexyloxy)-1,2,3,4-tetrahydrocarbazole-4-carboxylate (r-19);
t-20. benzyl 8-phenyl-1,2,3,4-tetrahydrocarbazole-4-carboxylate (r-20);
t-21. benzyl 8-phenoxy-1,2,3,4-tetrahydrocarbazole-4-carboxylate (r-21);
t-22. benzyl 6-methylthio-1,2,3,4-tetrahydrocarbazole-4-carboxylate (r-22);
t-23. benzyl 6-(trifluoromethyl)-1,2,3,4-tetrahydrocarbazole-4-carboxylate (r-23);
t-24. benzyl 6-(trichloromethyl)-1,2,3,4-tetrahydrocarbazole-4-carboxylate (r-24); and
t-25. benzyl 6-methyl-1,2,3,4-tetrahydrocarbazole-4-carboxylate (r-25).

The intermediate benzyl 9-H-1,2,3,4-tetrahydrocarbazole-4-carboxylates (t-1 to t-25) can be obtained by following in sequence procedures similar to those of Examples 34E to 34C inclusive but using equivalent amounts of the appropriate phenylbenzylamines, 9-benzyl-1,2,3,4-tetrahydrocarbazole-4-carboxylic acids and 1,2,3,4-tetrahydrocarbazole-4-carboxylic acids respectively. The corresponding phenylbenzylamines are prepared from the known corresponding anilines by the general procedure disclosed hereinabove.

Following a procedure similar to that of Example 35B but substituting for benzyl 1,2,3,4-tetrahydrocarbazole-4-carboxylate an equivalent amount of t-butyl 1,2,3,4-tetrahydrocarbazole-4-carboxylate and for 4-toluoyl chloride an equivalent amount of 4-benzyloxybenzoyl chloride there can be obtained
u-1. t-butyl 9-(4-benzyloxybenzoyl)-1,2,3,4-tetrahydrocarbazole-4-carboxylate,
which can be pyrolized, using the general procedure disclosed hereinabove, to give
u-2. 9-(4-benzyloxybenzoyl)-1,2,3,4-tetrahydrocarbazole-4-carboxylic acid,
which in turn can be hydrogenated according to the procedure disclosed hereinabove to give
9-(4-hydroxybenzoyl)-1,2,3,4-tetrahydrocarbazole-4-carboxylic acid (s-26 above).

The intermediate t-butyl-1,2,3,4-tetrahydrocarbazole-4-carboxylate (u-1) can be obtained from the corresponding free carboxylic acid using the known esterification procedure disclosed hereinabove.

Following a procedure similar to that of Example 35B but substituting for benzyl 1,2,3,4-tetrahydrocarbazole-4-carboxylate and for 4-toluoyl chloride equivalent amounts of t-butyl 6-benzyloxy-1,2,3,4-tetrahydrocarbazole-4-carboxylate and benzoyl chloride respectively there can be obtained
v-1. t-butyl 9-benzoyl-6-benzyloxy-1,2,3,4-tetrahydrocarbazole-4-carboxylate,
which can be pyrolized, using the general procedure disclosed hereinabove, to give
v-2. 9-benzoyl-6-benzyloxy-1,2,3,4-tetrahydrocarbazole-4-carboxylic acid,
which in turn can be hydrogenated according to the procedure disclosed hereinabove to give v-3. 9-benzoyl-6-hydroxy-1,2,3,4-tetrahydrocarbazole-4-carboxylic acid.

The intermediate t-butyl 6-benzyloxy-1,2,3,4-tetrahydrocarbazole-4-carboxylate can be obtained from t-butyl 6-hydroxy-1,2,3,4-tetrahydrocarbazole-4-carboxylate by reaction of its sodium salt (6-ONa) with benzyl bromide. The latter compound can be obtained from 6-hydroxy-1,2,3,4-tetrahydrocarbazole-4-carboxylic acid, using the known esterification procedure disclosed hereinabove, which in turn can be obtained by following procedures similar to those of Examples 34E and 34D but substituting for phenylbenzylamine an equivalent amount of 4-benzyloxyphenylbenzylamine and for 9-benzyl-1,2,3,4-tetrahydrocarbazole-4-carboxylic acid an equivalent amount of 9-benzyl-6-benzyloxy-1,2,3,4-tetrahydrocarbazole-4-carboxylic acid respectively.

Following a procedure similar to that of Example 34A but substituting for benzyl 9-benzoyl-1,2,3,4-tetrahydrocarbazole-4-carboxylate an equivalent amount of the following:
w-1. benzyl 9-benzoyl-4-methyl-1,2,3,4-tetrahydrocarbazole-4-carboxylate;
w-2. benzyl 9-benzoyl-3-methyl-1,2,3,4-tetrahydrocarbazole-4-carboxylate;
w-3. benzyl 9-benzoyl-2-methyl-1,2,3,4-tetrahydrocarbazole-4-carboxylate; and
w-4. benzyl 9-benzoyl-1-methyl-1,2,3,4-tetrahydrocarbazole-4-carboxylate;
there can be obtained respectively
x-1. 9-benzoyl-4-methyl-1,2,3,4-tetrahydrocarbazole-4-carboxylic acid;
x-2. 9-benzoyl-3-methyl-1,2,3,4-tetrahydrocarbazole-4-carboxylic acid;
x-3. 9-benzoyl-2-methyl-1,2,3,4-tetrahydrocarbazole-4-carboxylic acid; and
x-4. 9-benzoyl-1-methyl-1,2,3,4-tetrahydrocarbazole-4-carboxylic acid.

The intermediate benzyl 9-benzoyl-methyl-1,2,3,4-tetrahydrocarbazole-4-carboxylates (w-1 to w-4 above) can be obtained by following in sequence proceudres similar to those of Examples 34F to 34B inclusive but substituting respectively in Example 34F for ethyl cyclohexanone-2-carboxylate an equivalent amount of the following:
ethyl 2-methylcyclohexanone-2-carboxylate;
ethyl 3-methylcyclohexanone-2-carboxylate;
ethyl 4-methylcyclohexanone-2-carboxylate; and
ethyl 5-methylcyclohexanone-2-carboxylate;
and using in Examples 34E to 34B inclusive equivalent amounts of the corresponding ethyl 6-bromocyclohexanone-2-carboxylates, 9-benzyl-1,2,3,4-tetrahydrocarbazole-4-carboxylic acids, 1,2,3,4-tetrahydrocarbazole-4-carboxylic acids and benzyl 1,2,3,4-tetrahydrocarbazole-4-carboxylates respectively.

EXAMPLE 40

9-Benzoyl-6-hydroxy-1,2,3,4-tetrahydrocarbazole-3-carboxylic acid

A solution of 8.1 g. of 9-benzoyl-6-benzoyloxy-1,2,3,4-tetrahydrocarbazole-3-carboxylic acid in 250 ml. of ethyl acetate over 1.5 g. of 10 percent palladium-on-charcoal was subjected to a hydrogen atmosphere at about 40 psig while being heated with a heat lamp. The reaction was stopped when a theoretical amount of hydrogen had been adsorbed (1 hour) and the resulting cooled mixture was filtered and evaporated to dryness under reduced pressure. The residue was crystallized from acetone-n-hexane to yield 4.1 g. of the title compound; m.p. 224°–227°C.

EXAMPLE 41

9-(3-Fluorobenzoyl)-1,2,3,4-tetrahydrocarbazole-3-carboxylic acid

Following a procedure similar to that of Example 1B but using 8.7 g. of 1-(3-fluorobenzoyl)-1-phenylhydrazine hydrochloride and 5.0 g. of cyclohexanone-4-carboxylic acid there was obtained 9.2 g. of the title compound; m.p. 170°–171°C.

EXAMPLE 42

9-(4-Phenylbenzoyl)-1,2,3,4-tetrahydrocarbazole-3-carboxylic acid

Following a procedure similar to that of Example 1B but using 13.5 g. of 1-(4-phenylbenzoyl)-1-phenylhydrazine hydrochloride and 6.86 g. of cyclohexanone-4-carboxylic acid there was obtained 12 g. of the title compound; m.p. 212°–213°C. (acetone-water).

EXAMPLE 43

9-Benzoyl-8-fluoro-1,2,3,4-tetrahydrocarbazole-3-carboxylic acid

A solution of 6.4 g. benzaldehyde 1-benzoyl-1-(2-fluorophenyl)hydrazone and 5.35 g. of cyclohexanone-4-carboxylic acid in 50 ml. glacial acetic acid and 10 ml. of glacial acetic acid saturated with hydrogen chloride was heated under reflux for two hours. An additional 10 ml. glacial acetic acid saturated with hydrogen chloride was then added and heating under reflux was continued two additional hours. A further 5 ml. glacial acetic acid saturated with hydrogen chloride was added and heating under reflux was continued another two hours. The mixture was cooled, 25 ml. water was added portion-wise, and the resulting solid was collected by filtration and washed with water to yield 3.54 g. of the title compound; m.p. 250°–251°C. (acetic acid-water).

The benzaldehyde 1-benzoyl-1-(2-fluorophenyl) hydrazone was prepared as follows: A stirred solution of 2.1 g. of benzaldehyde (2-fluorophenyl)hydrazone in 40 ml. dry dimethylformamide was treated with 0.23 g. sodium hydride in a nitrogen atmosphere with water-bath cooling. When hydrogen evolution had ceased, there was added dropwise a solution of 1.2 ml. of benzoyl chloride in a small amount of dry dimethylformamide and stirring as continued for 3 hours. To this mixture was added enough glacial acetic acid to neutralize any excess alkali, water, and ether. The ether extract was washed with water several times, dried, and evaporated to dryness under reduced pressure to yield 1.7 g. of benzaldehyde 1-benzoyl-1-(2-fluorophenyl)-hydrazone; m.p. 97°–99°C. (ethyl alcohol-water).

EXAMPLE 44

9-Benzoyl-8-bromo-1,2,3,4-tetrahydrocarbazole-3-carboxylic acid

A solution of acetaldehyde 1-benzoyl-1-(2-bromophenyl)hydrazone, prepared from 11 g. of acetaldehyde 2-bromophenyl hydrazone (see below), and 9.16 g. of cyclohexanone-4-carboxylic acid in 25 ml. glacial acetic acid was heated on a hot plate until evolution of acetaldehyde was no longer detected (about two hours), 25 ml. glacial acetic acid saturated with hydrogen chloride was added and heating was continued for 30 minutes. The mixture was cooled and cautiously diluted with water, and the resulting solid was collected by filtration and washed with water to give 2.24 g. of the title compound; m.p. 196°–198°C. (chloroform-heptane).

The acetaldehyde 1-benzoyl-1-(2-bromophenyl) hydrazone was prepared as follows: A solution of 11.2 g. of 2-bromophenyl hydrazine in ether was treated with 7 ml. of acetaldehyde and allowed to stand for 1 hour with occasional swirling. The ether solution was washed with water, a small amount of dilute potassium bicarbonate solution, and saturated sodium chloride solution, dried over magnesium sulfate and evaporated to dryness under reduced pressure. The residue was taken up in 25 ml. dry dimethylformamide and the resulting solution was added dropwise, with stirring and water-bath cooling, to a mixture of 1.56 g. of sodium hydride in 25 ml. dry dimethylformamide and stirring was continued for 1 hour. To this solution under nitrogen was added dropwise with stirring a solution of 7 ml. of benzoyl chloride in 10 ml. of dimethylformamide and stirring was continued for 4 hours. The mixture was diluted with ether and treated with water containing sufficient glacial acetic acid to neutralize excess alkali. The ether extract was washed with water, dilute potassium carbonate solution, water, and saturated sodium chloride solution, dried over magnesium sulfate and evaporated to dryness under reduced pressure to give acetaldehyde 1-benzoyl-1-(2-bromophenyl) hydrazone which was used as such in the above reaction.

EXAMPLE 45

Pivaloyloxymethyl 9-benzoyl-1,2,3,4-tetrahydrocarbazole-3-carboxylate

A mixture of 12.8 g. of 9-benzoyl-1,2,3,4-tetrahydrocarbazole-3-carboxylic acid, 20 g. of potassium bicarbonate, 12 ml. of chloromethyl pivalate in 50 ml. of dry dimethylformamide was stirred and heated on a steambath for two hours. The mixture was cooled and diluted with ether, the ether mixture was washed several times with water, dried over magnesium sulfate, and evaporated under reduced pressure to dryness to give 10.6 g. of the title compound; m.p. 75°–77°C. (methyl alcohol).

EXAMPLE 46

Benzoyloxymethyl 9-benzoyl-1,2,3,4-tetrahydrocarbazole-3-carboxylate

Following the procedure similar to that of Example 45 but using 12.8 g. of 9-benzoyl-1,2,3,4-tetrahydrocarbazole-3-carboxylic acid, 20 g. of potassium bicarbonate, 10 ml. of chloromethyl benzoate in 50 ml. of dry dimethylformamide there was obtained, after filtration of the ether extract through silica gel followed by combination of those fractions showing only one identical spot on thin layer chromotography and evaporation to dryness under reduced pressure, 14 g. of the title compound; m.p. 84°–86°C. (methyl alcohol).

EXAMPLE 47

4-Acetamidophenyl 9-benzoyl-1,2,3,4-tetrahydrocarbazole-3-carboxylate

A solution of 9.6 g. of 9-benzoyl-1,2,3,4-tetrahydrocarbazole-3-carboxylic acid, 15 ml. of thionyl chloride and two drops of dry dimethylformamide in 100 ml.

of ethylene dichloride was stirred at room temperature for 7 hours. The mixture was evaporated to dryness under reduced pressure, at room temperature, and to the resulting residue was added a solution of 6 g. of 4-acetamidophenol in 50 ml. of dry pyridine. The solution was stirred at room temperature for 30 minutes and diluted with water. The resulting solid was collected by filtration to give 6.74 g. of the title compound; m.p. 166°–168°C. (ethyl alcohol).

Following procedures similar to that of Examples 45, 46 and 47 but substituting in each case for 9-benzoyl-1,2,3,4-tetrahydrocarbazole-3-carboxylic acid an equivalent amount of 9-benzoyl-1,2,3,4-tetrahydrocarbazole-4-carboxylic acid there are obtained respectively:

y-1. pivaloyloxymethyl 9-benzoyl-1,2,3,4-tetrahydrocarbazole-4-carboxylate;
y-2. benzoyloxymethyl 9-benzoyl-1,2,3,4-tetrahydrocarbazole-4-carboxylate; and
y-3. 4-acetamidophenyl 9-benzoyl-1,2,3,4-tetrahydrocarbazole-4-carboxylate.

Following a procedure similar to that of Example 45 but substituting for chloromethyl pivalate an equivalent amount of
chloromethyl 3-(trifluoromethyl)benzoate;
chloromethyl 4-t-butylbenzoate;
chloromethyl 4-toluate;
chloromethyl 4-fluorobenzoate;
chloromethyl 3-anisoate;
chloromethyl 4-ethoxy-3-fluorobenzoate;
chloromethyl 2,4-dichlorobenzoate;
chloromethyl 4-nitrobenzoate; and
chloromethyl 4-trifluoromethoxybenzoate
there can be obtained respectively:
z-1. 3-(trifluoromethyl)benzoyloxymethyl 9-benzoyl-1,2,3,4-tetrahydrocarbazole-3-carboxylate;
z-2. 4-t-butylbenxoyloxymethyl 9-benzoyl-1,2,3,4-tetrahydrocarbazole-3-carboxylate;
z-3. 4-toluoyloxymethyl 9-benzoyl-1,2,3,4-tetrahydrocarbazole-3-carboxylate;
z-4. 4-fluorobenzoyloxymethyl 9-benzoyl-1,2,3,4-tetrahydrocarbazole-3-carboxylate;
z-5. 3-anisoyloxymethyl 9-benzoyl-1,2,3,4-tetrahydrocarbazole-3-carboxylate;
z-6. 4-ethoxy-3-fluorobenzoyloxymethyl 9-benzoyl-1,2,3,4-tetrahydrocarabazole-3-carboxylate;
z-7. 2,4-dichlorobenzoyloxymethyl 9-benzoyl-1,2,3,4-tetrahydrocarbazole-3-carboxylate;
z-8. 4-nitrobenzoyloxymethyl 9-benzoyl-1,2,3,4-tetrahydrocarbazole-3-carboxylate; and
z-9. 4-trifluoromethoxybenzoyloxymethyl 9-benzoyl-1,2,3,4-tetrahydrocarbazole-3-carboxylate.

EXAMPLE 48

9-Benzoyl-3hydroxymethyl-1,2,3,4-tetrahydrocarbazole

1Benzoyl-1phenylhydrazine hydrochloride (23.8 g.) and 18 g. of 4-hydroxymethylcyclohexanone ethylene ketal in 450 ml. of absolute ethyl alcohol was heated under reflux for four hours. The chilled mixture was filtered, the filtrate was evaporated to dryness under reduced pressure and the resulting residue was dissolved in ether. The ether solution was washed with water, dilute hydrochloric acid, water, dilute sodium bicarbonate, and water, dried and evaporated to dryness to give, after recrystallization from ethyl acetate-hexane, 9.6 g. of 9-benzoyl-3-hydroxymethyl-1,2,3,4-tetrahydrocarbazole; m.p. 105°–107°C.

Preparation of 4-Hydroxymethylcyclohexanone ethylene ketal

Ethyl cyclohexanone-4-carboxylate (335 g.), 550 ml. ethylene glycol and 21 g. of p-toluenesulfonic acid in 5.5 liters of benzene were heated at reflux with stirring for 24 hours while water was separated by means of a water trap. The mixture was cooled and poured into 4 liters of ice water. The benzene layer was separated, washed with 1 liter of 5% sodium bicarbonate, 1 liter of water and 1 liter of saturated sodium chloride solution, dried and evaporated to dryness to give, after distillation, 245.6 g. of ethyl cyclohexanone-4-carboxylate ethylene ketal; b.p. 95-99.5°C. (0.07 mm.); $N^{25}$ D 1.4620. A solution of 35 g. of the ketal-ester in 50 ml. of dry tetrahydrofuran was added dropwise to 5.7 g. of lithium aluminum hydride in 250 ml. of dry tetrahydrofuran, and the mixture was heated at reflux for 5 hours and cooled to room temperature. A saturated sodium chloride solution (11.4 ml.) was added dropwise and heating at reflux was continued for one hour. The mixture was cooled and filtered, and the filtrate was dried and evaporated to dryness to give 26.9 g. of 4-hydroxymethylcyclohexanone ethylene ketal as a clear, colorless oil which was used without further purification.

9-Benzoyl-3-hydroxymethyl-1,2,3,4-tetrahydrocarbazole was found to be active when tested in rats at 100 mg./kg. of body weight in the Inhibition of Carrageenin-Induced Foot Edema and Adjuvant-Induced Arthritis Test Procedures described hereinbefore and is indicated for use as an antiinflammatory agent. This compound can be prepared for use following procedures described hereinabove for compounds having formulas I and II.

EXAMPLE 49

9-Benzoyl-3-(N-phenylcarbamoyloxymethyl)-1,2,3,4-tetrahydrocarbazole

9-Benzoyl-3-hydroxymethyl-1,2,3,4-tetrahydrocarbazole (9.8 g.) and phenylisocyanate (4.2 g.) were combined and heated on a steam bath for 1½ hours. The mixture was cooled and triturated in ether and the resulting solid was collected by filtration and washed with ether to give 7.1 g. of the title compound; m.p. 140°–143°C.

9-Benzoyl-3-(N-phenylcarbonyloxymethyl)-1,2,3,4-tetrahydrocarbazole, when tested in the Autotiter method described by Goss et al., Applied Microbiology 16 (No. 9), 1414-1416 (1968), was found to be antibacterially effective against Pseudomonas aeruginosa at a concentration of 125 mcg./ml. thus indicating the utility of this compound as an antibacterial agent against Pseudomonas aeruginosa. This compound may be formulated for use by conventional procedures, e.g., for application to inanimate surfaces; it can be formulated as a dilute solution in an aqueous medium or in a solution containing a surfactant and is applied to the surface to be disinfected by conventional means such as spraying, swabbing, immersion and the like.

EXAMPLE 50

9-(2-Thenoyl)-1,2,3,4-tetrahydrocarbazole-3-carboxylic acid

To 22 ml. of phenylhydrazine in 22 ml. of ether was added 22 ml. of acetaldehyde, gentle reflux being maintained with external cooling, and the solution was allowed to stand for one-half hour. Benzene was added and the solution was dried over magnesium sulfate, filtered, dried over calcium sulfate, and evaporated to dryness under reduced pressure below 35°C. The residue was dissolved in pentane and the mixture was chilled and filtered to give 6.9 g. of acetaldehyde phenylhydrazine, a cold solution of which in 20 ml. pyridine was treated dropwise with 7.33 g. of 2-thienylcarbonyl chloride. The solution was warmed to room temperature, diluted with water and extracted with ether. The ether extract was washed with water, dilute acetic acid, water, sodium carbonate solution and water, dried and evaporated to dryness. The acetaldehyde 1-(2-thenoyl)-1-phenylhydrazone was dissolved in absolute ethyl alcohol, 15 ml. of a 4-N solution of hydrogen chloride in absolute ethyl alcohol was added, and the solution was diluted with ether, chilled and filtered and the filtrate was evaporated to dryness under reduced pressure. A solution of the crude 1-(2-thenoyl)-1-phenylhydrazine hydrochloride in acetic acid containing 5 ml. of acetic acid saturated with hydrogen chloride was added to 3.1 g. of cyclohexanone-4-carboxylic acid and the mixture was warmed on a steam bath for about two hours, cooled to room temperature, diluted with 10 ml. of water and chilled. The resulting precipitate was collected, washed with 75% acetic acid in water and dried to yield 4.7 g. of the title compound; m.p. 180°–182°C.

EXAMPLE 51

9-Cyclohexanecarbonyl-1,2,3,4-tetrahydrocarbazole-3-carboxylic acid

To a stirred mixture of 3.88 g. of sodium hydride in 100 ml. of dimethylformamide was added portionwise 20 g. of acetaldehyde phenylhydrazine, stirring was continued for 2 hours, 22 g. of cyclohexanecarbonyl chloride was added dropwise, stirring was continued for three hours and the reaction mixture was then poured into ice water containing acetic acid. The aqueous mixture was extracted with ether and the ether extract was washed with water, dried and evaporated to dryness. The residue was taken up in absolute ethyl alcohol and ether, hydrogen chloride in ethyl alcohol was added, and the solution was allowed to stand 1 hour, chilled, and evaporated to dryness under reduced pressure. The residue was triturated with ethyl acetate and the resulting solid was filtered to yield 9.2 g. of 1-cyclohexanecarbonyl-1-phenylhydrazine hydrochloride; m.p. 170°–172°C. This was combined with 5.5 g. of cyclohexanone-4-carboxylic acid in 100 ml. of glacial acetic acid and the mixture was heated at the boiling point for 1 hour, diluted with 50 ml. of water and chilled. The resulting precipitate was collected by filtration, washed with 75% acetic acid in water and dried to yield 3.9 g. of the title compound; m.p. 157°–159°C.

EXAMPLE 52

9-Benzoyl-5-(and 7)-bromo-6-methoxy-1,2,3,4-tetrahydrocarbazole

A suspension of 7.0 g. of 9-benzoyl-6-methoxy-1,2,3,4-tetrahydrocarbazole (Example 21) in glacial acetic acid was treated dropwise at room temperature with 1.6g. of bromine in acetic acid (total volume of acetic acid 100 ml.). When addition was complete the solvent was evaporated under reduced pressure and the solid residue was recrystallized from acetone and dimethylformamide-aqueous acetone to give 3.5 g. of the title compound, m.p. 242°–245°C. (which was determined by NMR to be approximately a 1/1 mixture of the 5-and 7-bromo isomers).

We claim:
1. A compound having the formula

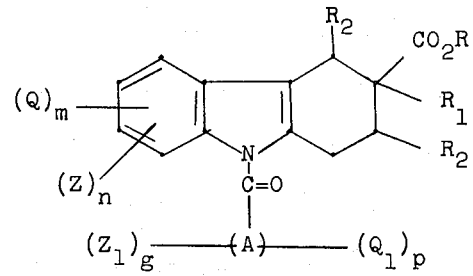

wherein:
A. represents 2-thienyl;
Q and $Q_1$ represents substituents selected from lower-alkyl, phenyl-lower-alkyl, lower-alkoxy, phenyl lower-alkoxy, phenoxy, phenyl, di(lower-alkyl)-amino, lower-alkanoylamino, trihalomethyl, trihalomethoxy, halo and hydroxy, where phenyl is unsubstituted or substituted by from one to three of the same or different substituents selected from lower-alkyl, lower-alkoxy, trihalomethyl and halo;
Z and $Z_1$ represent substituents selected from lower-alkylthio, lower-alkylsulfinyl, lower-alkylsulfonyl, amino and nitro;
$m$ represents an integer from 0 to (3-n) inclusive;
$p$ represents an integer from 0 to (3-g) inclusive;
$n$ and $g$ represent integers from 0 to 1 inclusive;
R represents hydrogen, lower-alkyl, 4-acetamidophenyl, lower-alkanoyloxymethyl, benzoyloxymethyl or benzoyloxymethyl substituted on phenyl by from one or two of the same or different substituents selected from lower-alkyl, lower-alkoxy, trihalomethyl, nitro and halo; and
$R_1$ and $R_2$ each represent hydrogen or methyl, at least one of which is hydrogen; or
$(Q)_m$ taken together with $(Z)_n$, or $(Q_1)_p$ taken together with $(Z_1)_g$ represents methylenedioxy attached to adjacent carbon atoms.

2. A compound having the formula

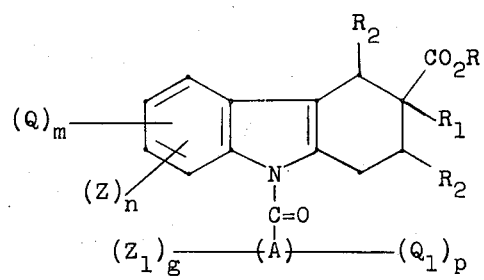

wherein:
A. represents cyclohexyl;
Q and $Q_1$ represent substituents selected from lower-alkyl, phenyl-lower-alkyl, lower-alkoxy, phenyl-lower-alkoxy, phenoxy, phenyl, di(lower-alkyl)-amino, lower-alkanoylamino, trihalomethyl, trihalomethoxy, halo and hydroxy, where phenyl is unsubstituted or substituted by from one to three of the same or different substituents selected from lower-alkyl, lower-alkoxy, trihalomethyl and halo;

Z and $Z_1$ represent substituents selected from lower-alkylthio, lower-alkylsulfinyl, lower-alkyl-sulfonyl, amino and nitro;

m represents an integer from 0 to (3-n) inclusive;
p represents an integer from 0 to (3-g) inclusive;
n and g represent integers from 0 to 1 inclusive;
R represents hydrogen, lower-alkyl, 4-acetamidophenyl, lower-alkanoyloxymethyl, benzoyloxymethyl or benzoyloxymethyl substituted on phenyl by from one or two of the same or different substituents selected from lower-alkyl, lower-alkoxy, trihalomethyl, nitro and halo; and
$R_1$ and $R_2$ each represent hydrogen or methyl, at least one of which is hydrogen; or
$(Q)_m$ taken together with $(Z)_n$, or $(Q_1)_p$ taken together with $(Z_1)_g$ represents methylenedioxy attached to adjacent carbon atoms.

3. 9-(2-Thenoyl)-1,2,3,4-tetrahydrocarbazole-3-carboxylic acid according to claim 1.

4. 9-Cyclohexanecarbonyl-1,2,3,4-tetrahydrocarbazole-3-carboxylic acid according to claim 2.

5. 4-Acetamidophenyl 9-benzoyl-1,2,3,4-tetrahydrocarbazole-3-carboxylate.

6. A compound having the formula

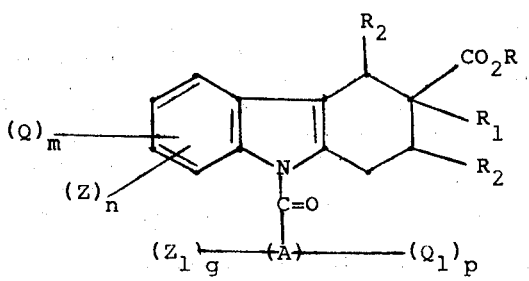

wherein:
A. represents phenyl or naphthyl;
Q and $Q_1$ represent substituents selected from lower-alkyl, lower-alkoxy, benzyloxy, phenyl, trihalomethyl and hydroxy;
Z and $Z_1$ represent substituents selected from lower-alkylthio, lower-alkylsulfinyl, lower-alkylsulfonyl, amino and nitro;
m represents an integer from 0 to (3-n) inclusive;
p represents an integer from 0 to (3-g) inclusive;
n and g represent the integer 0; and
R, $R_1$ and $R_2$ each represent hydrogen; or
$(Q)_m$ taken together with $(Z)_n$, or $(Q_1)_p$ taken together with $(Z_1)_g$ represents methylenedioxy attached to adjacent carbon atoms.

7. A compound according to claim 6 wherein (A) represents phenyl.

8. A compound according to claim 7 wherein m and p represent integers from 0 to 1 inclusive.

9. A compound according to claim 8 wherein Q and $Q_1$ represent substituents selected from lower-alkyl and lower-alkoxy.

10. A compound according to claim 9 wherein a substituent represented by Q occurs at the 6-position of the tetrahydrocarbazole ring; and a substituent represented by $Q_1$ occurs at the 4-position of phenyl.

11. 9-Benzoyl-1,2,3,4-tetrahydrocarbazole-3-carboxylic acid according to claim 10.

12. 9-(4-Toluoyl)-1,2,3,4-tetrahydrocarbazole-3-carboxylic acid according to claim 10.

13. 9-(4-Anisoyl)-1,2,3,4-tetrahydrocarbazole-3-carboxylic acid according to claim 10.

14. 9-(4-Anisoyl)-6-methyl-1,2,3,4-tetrahydrocarbazole-3-carboxylic acid according to claim 10.

15. 9-Benzoyl-6-methoxy-1,2,3,4-tetrahydrocarbazole-3-carboxylic acid according to claim 10.

16. 9-Benzoyl-6-methyl-1,2,3,4-tetrahydrocarbazole-3-carboxylic acid according to claim 10.

17. A compound having the formula

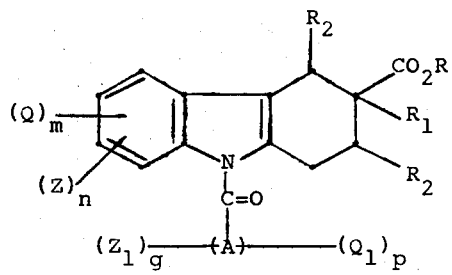

wherein:
A. represents phenyl or naphthyl;
Q and $Q_1$ represent substituents selected from lower-alkyl and halo, at least one of which is halo;
Z and $Z_1$ represent substituents selected from lower-alkylthio, lower-alkylsulfinyl, lower-alkyl-sulfonyl, amino and nitro;
m and p represent integers from 0 to 1 inclusive;
n and g represent the integer 0; and
R, $R_1$ and $R_2$ each represent hydrogen; or
$(Q)_m$ taken together with $(Z)_n$, or $(Q_1)_p$ taken together with $(Z_1)_g$ represents methylenedioxy attached to adjacent carbon atoms.

18. A compound according to claim 17 wherein (A) represents phenyl.

19. 9-(4-Fluorobenzoyl)-1,2,3,4-tetrahydrocarbazole-3-carboxylic acid according to claim 18.

20. 9-(4-Chlorobenzoyl)-1,2,3,4-tetrahydrocarbazole-3-carboxylic acid according to claim 18.

21. 9-Benzoyl-6-fluoro-1,2,3,4-tetrahydrocarbazole-3-carboxylic acid according to claim 18.

22. 9-(3-Chlorobenzoyl)-1,2,3,4-tetrahydrocarbazole-3-carboxylic acid according to claim 18.

23. 9-(3-Fluorobenzoyl)-1,2,3,4-tetrahydrocarbazole-3-carboxylic acid according to claim 18.

24. A compound having the formula

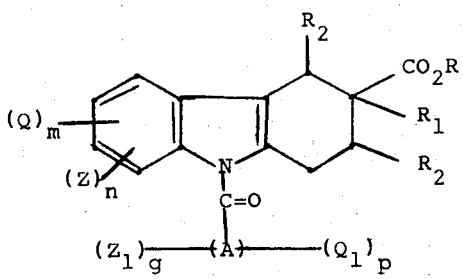

wherein (A) represents phenyl or naphthyl;

Q and Q₁ represent substituents selected from lower-alkyl, phenyl-lower-alkyl, lower-alkoxy, phenyl-lower-alkoxy, phenoxy, phenyl, di(lower-alkyl)-amino, lower-alkanoylamino, trihalomethyl, trihalomethoxy, halo and hydroxy, where phenyl is unsubstituted or substituted by from one to three of the same or different substituents selected from lower-alkyl, lower-alkoxy, trihalomethyl and halo;

Z and $Z_1$ represent substituents selected from lower-alkylthio, lower-alkylsulfinyl, lower-alkyl-sulfonyl, amino and nitro;

$m$ represents an integer from 0 to (3-n) inclusive;
$p$ represents an integer from 0 to (3-g) inclusive;
$n$ and $g$ represent integers from 0 to 1 inclusive;
R represents lower-alkanoyloxymethyl, benzoyloxymethyl or benzoyloxymethyl substituted on phenyl by from one or two of the same or different substituents selected from lower-alkyl, lower-alkoxy, trihalomethyl, nitro and halo; and
$R_1$ and $R_2$ each represent hydrogen or methyl, at least one of which is hydrogen; or
$(Q)_m$ taken together with $(Z)_n$, or $(Q_1)_p$ taken together with $(Z_1)_g$ represents methylenedioxy attached to adjacent carbon atoms.

25. Pivaloyloxymethyl 9-benzoyl-1,2,3,4-tetrahydrocarbazole-3-carboxylate according to claim 24.

26. Benzoyloxymethyl 9-benzoyl-1,2,3,4-tetrahydrocarbazole-3-carboxylate according to claim 24.

27. A compound having the formula

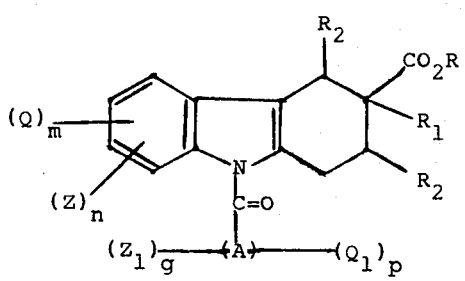

wherein:
(A) represents phenyl or naphthyl;
Q and $Q_1$ represent lower-alkyl;
Z and $Z_1$ represent substituents selected from lower-alkylthio, lower-alkylsulfinyl, lower-alkyl-sulfonyl, amino and nitro;
$g, m, n,$ and $p$ represent integers from 0 to 1 inclusive;
R represents hydrogen or lower-alkyl;
$R_1$ represents hydrogen or methyl; and
$R_2$ represents hydrogen; or
$(Q)_m$ taken together with $(Z)_n$, or $(Q_1)_p$ taken together with $(Z_1)_g$ represents methylenedioxy attached to adjacent carbon atoms.

28. Ethyl 9-(4-toluoyl)-1,2,3,4-tetrahydrocarbazole-3-carboxylate according to claim 27.

29. Ethyl 9-benzoyl-1,2,3,4-tetrahydrocarbazole-3-carboxylate according to claim 27.

30. 9-(3,4-Methylenedioxybenzoyl)-1,2,3,4-tetrahydrocarbazole-3-carboxylic acid according to claim 27.

31. A compound having the formula

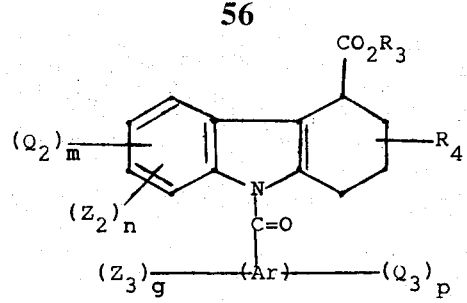

wherein:
(Ar) represents phenyl or naphthyl;
$Q_2$ and $Q_3$ represent substituents selected from lower-alkyl and lower-alkoxy;
$Z_2$ and $Z_3$ represent lower-alkylthio;
$m$ represents an integer from 0 to (3-n) inclusive;
$p$ represents an integer from 0 to (3-g) inclusive;
$n$ and $g$ represent the integer 0; and
$R_3$ and $R_4$ represent hydrogen; or
$(Q_2)_m$ taken together with $(Z_2)_n$, or $(Q_3)_p$ taken together with $(Z_3)_g$ represent methylenedioxy attached to adjacent carbon atoms.

32. A compound according to claim 31 wherein (Ar) represents phenyl.

33. A compound according to claim 32 wherein $m$ and $p$ represent an integer from 0 to 1 inclusive.

34. A compound according to claim 33 wherein a substituent represented by $Q_2$ occurs at the 6-position of the tetrahydrocarbazole ring; and a substituent represented by $Q_3$ occurs at the 4-position of phenyl.

35. 9-Benzoyl-1,2,3,4-tetrahydrocarbazole-4-carboxylic acid according to claim 34.

36. 9-(4-Toluoyl)-1,2,3,4-tetrahydrocarbazole-4-carboxylic acid according to claim 34.

37. 9-Benzoyl-6-methoxy-1,2,3,4-tetrahydrocarbazole-4-carboxylic acid according to claim 34.

38. 9-Benzoyl-6-methyl-1,2,3,4-tetrahydrocarbazole-4-carboxylic acid according to claim 34.

39. A compound having the formula

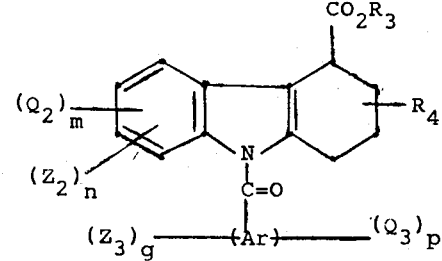

wherein:
(Ar) represents phenyl or naphthyl;
$Q_2$ and $Q_3$ represent halo;
$Z_2$ and $Z_3$ represent lower-alkylthio;
$m$ and $p$ represent an integer from 0 to 1 inclusive;
$n$ and $g$ represent the integer 0; and
$R_3$ and $R_4$ represent hydrogen; or
$(Q_2)_m$ taken together with $(Z_2)_n$, or $(Q_3)_p$ taken together with $(Z_3)_g$ represent methylenedioxy attached to adjacent carbon atoms.

40. A compound according to claim 39 wherein (Ar) is phenyl.

41. 9-(4-Chlorobenzoyl)-1,2,3,4-tetrahydrocarbazole-4-carboxylic acid according to claim 40.

* * * * *